US010513741B2

(12) United States Patent
Ji et al.

(10) Patent No.: US 10,513,741 B2
(45) Date of Patent: Dec. 24, 2019

(54) **COMPOSITIONS AND METHODS FOR DETECTION OF *MYCOBACTERIUM AVIUM* PARATUBERCULOSIS**

(71) Applicant: Life Technologies Corporation, Carlsbad, CA (US)

(72) Inventors: Yongmei (Alexis) Ji, Chicago, IL (US); Pius Brzoska, Woodside, CA (US); Angela Burrell, Austin, TX (US); Craig Cummings, Pacifica, CA (US); Catherine O'Connell, Austin, TX (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 15 days.

(21) Appl. No.: 15/891,454

(22) Filed: Feb. 8, 2018

(65) Prior Publication Data

US 2018/0237830 A1    Aug. 23, 2018

Related U.S. Application Data

(60) Division of application No. 14/978,243, filed on Dec. 22, 2015, now Pat. No. 9,926,609, which is a continuation of application No. 13/785,409, filed on Mar. 5, 2013, now Pat. No. 9,255,299.

(60) Provisional application No. 61/619,196, filed on Apr. 2, 2012.

(51) Int. Cl.
| C12P 19/34 | (2006.01) |
| C12Q 1/689 | (2018.01) |
| C12Q 1/6806 | (2018.01) |

(52) U.S. Cl.
CPC ........... *C12Q 1/689* (2013.01); *C12Q 1/6806* (2013.01); *C12Q 2600/112* (2013.01); *C12Q 2600/16* (2013.01)

(58) Field of Classification Search
None
See application file for complete search history.

(56) References Cited

U.S. PATENT DOCUMENTS

| 7,108,968 | B2 | 9/2006 | Gingeras et al. |
| 9,255,299 | B2 | 2/2016 | Ji et al. |
| 9,926,609 | B2 | 3/2018 | Ji et al. |
| 2007/0042383 | A1 | 2/2007 | Kapur et al. |
| 2007/0105167 | A1 | 5/2007 | Ausubel et al. |
| 2013/0260374 | A1 | 10/2013 | Ji et al. |
| 2013/0260375 | A1 | 10/2013 | Cummings et al. |

FOREIGN PATENT DOCUMENTS

| EP | 1371985 | 12/2003 |
| WO | WO2008119332 | 10/2008 |
| WO | WO2013/151647 | 10/2013 |
| WO | WO2013/151648 | 10/2013 |

OTHER PUBLICATIONS

Rychlik et al., Nucleic Acids Research 17(21), 8543-8551 (1989). (Year: 1989).*
Alvarez, et al., "Genetic Diversity of *Mycobacterium avium* Isolates Recovered from Clinical Samples and from the Environment: Molecular Characterization for Diagnostics Purposes", *Journal of Clinical Microbiology*, vol. 46, No. 4, Feb. 13, 2008, 1246-1251.
Bartos, et al., "Identification of members of *Mycobaterium avium* species by Accu-Probes, serotyping, and single IS900, IS901, IS1245 and IS901-flanking region PCR with internal standards", *Journal Microbiological Methods*, vol. 64, No. 3, 2006, 333-345.
Cayrou, et al., "Genotyping of *Mycobacterium avium* complex organisms using multispacer sequence typing", *Microbiology*, vol. 156, No. 3, Mar. 1, 2010, 687-694.
Covert, et al., "Occurrence of nontuberculous mycobacteria in environmental samples", *Applied and Environmental Microbiology*, vol. 65, No. 5, Jun. 1999, 2492-2496.
EP18174660.3, Search Report, dated Jul. 17, 2018, 1-8.
Falkinham, et al., "Factors influencing numbers of *Mycobacterium avium*, *Mycobacterium intracellulare*, and other mycobacteria in drinking water distribution systems", *Applied and Environmenta Microbiology*, vol. 67, No. 3, Jun. 2001, 1225-1231.
Higgins, et al., "Identification of *Mycobacterium* spp. of veterinary importance using rpOB gene sequencing", *BMC Veterinary Research*, vol. 7, No. 1, Jan. 1, 2011, 1-14.
Hilborn, et al., "Molecular comparison of *Mycobacterium avium* isolates from clinical and environmental sources", *Applied and Environmental Microbiology*, vol. 74, No. 15, Aug. 2008, 4966-4968.
Johansen, et al., "Distribution of IS1311 and IS1245 in *Mycobacterium avium* Subspecies Revisited", *Jounal of Clinical Microbiological*, vol. 45, No. 5, May 1, 2005, 2500-2502.
Le Dantec, et al., "Occurrence of Mycobacteria in Water Treatment Lines and in Water Distribution Systems", *Applied and Environmenta Microbiology*, vol. 68, No. 11, Nov. 2002, 5318-5325.
Pate, et al., "IS1245 RFLP-based genotyping study of *Mycobacterium avium* subsp. *hominissuis* isolates from pigs and humans", *Comparative Immunology, Microbiology & Infectious Diseases*, vol. 31, No. 6, Nov. 1, 2008, 537-550.
PCT/US2013/029072, , "International Preliminary Report on Patentability and Written Opinion dated Oct. 7, 2014", Oct. 7, 2014, 8 Pages.
PCT/US2013/029072, , "International Search Report and Written Opinion", dated May 29, 2013, 1-14.
PCT/US2013/029093, , "International Preliminary Report on Patentability and Written Opinion dated Oct. 7, 2014", Oct. 7, 2014, 7 Pages.
PCT/US2013/029093, , "International Search Report and Written Opinion", dated May 27, 2013, 1-13.

(Continued)

*Primary Examiner* — Kenneth R Horlick

(57) ABSTRACT

Disclosed are compositions, assays, methods, diagnostic methods, kits and diagnostic kits for the specific and differential detection of *Mycobacterium avium* subsp. *paratuberculosis* from samples including veterinary samples, clinical samples, food samples, forensic sample, an environmental sample (e.g., soil, dirt, garbage, sewage, air, or water), including food processing and manufacturing surfaces, or a biological sample.

1 Claim, No Drawings

Specification includes a Sequence Listing.

(56) References Cited

OTHER PUBLICATIONS

Ravva, et al., "Real-time quantitative PCR detection of *Mycobacterium avium* subsp. *paratuberculosis* and differentiation from other mycobacteria using SYBR Green and TaqMan assays", *Journal of Microbiology Methods*, vol. 63, May 31, 2005, 305-317.
Santos, et al., "Detection and identification of mycobacteria in the Lisbon water distribution system", *Water and Science Technology*, vol. 52, No. 8, 2005, 177-180.
Shin, et al., "Efficient Differentiation of *Mycobacterium avium* Complex Species and Subspecies by Use of Five-Target Multiplex PCR", *Journal of Clinical Microbiology*, vol. 48, No. 11, Nov. 2010, 4057-4062.
Stratagene, "Gene Characterization Kits", 1988, 38-39.

* cited by examiner

SEQUENCE LISTING

<160> NUMBER OF SEQ ID NOS: 50

<210> SEQ ID NO 1
<211> LENGTH: 1863
<212> TYPE: DNA
<213> ORGANISM: Mycobacterium avium

<400> SEQUENCE: 1

```
cgggtgcgga ttgatcagcc gcccatgggc caccagcgat ccgtgttgct tgagccgctg      60
ggtgcggacg ttgacctcgt agccgagcac cccgtcgagc tggccgagtt gctcgcgcag     120
gtagcggtac aggtcgtcgg aatctcggca gatggccacg gccatcaggt ttttggatcc     180
gcttgtggcg ccggcgaaag caatctgcgg atgggccgcg atacgttcgc cgaccgtgtg     240
cacgtcgcga ggcgcaaccg tgagccacag catggcgctg aggcgatggc cgagccgttc     300
gggtagtacg tcgacgtcgt agaccagggc gccgcaggcc tccagcgccg cgatccgcct     360
gctcacccgc gccaccgacc aaccggtgcg cgcggccagt tgggactgcg gagtgcggcc     420
gtcgtcggcg agcgccgcga gcagcgggcg gtcttcggcg gtgggccggg accggtgagt     480
tcccgactcc ggctgggccc gcgcggccac gatccgctgc gcttgccggt ccgagagcgc     540
gctgccgtag cccgtccagg gcgcgttcac cgggtcgccg aacgaatgca gcatcagatc     600
gatgctgatg tcggtgaccg cggcggtgcg cggtaggagc tgcgtcagca ggtcctcgcg     660
ggtgtcgccc agcggcgcac ggatgacgca gaccaggtcg gtccacccg ccagcacatt     720
ggcgtgggac acgtcggggc gtcgcaccag cgcgtcggcc agccgcgata tgcggtccgg     780
```

```
cgccgcacgg atgcggcaca cccagtccgc gtcgccatcg gcccaccggt tctccagccc    840
gacgacgcgc accaccccgt cgcggcgcag ccggtgatac cgccgggcga ccgtctgctc    900
ggtggcgccc accacgctgg cgatccggcg aaacgagacc cggggagcta actgcagggc    960
gtgcagaatc tgtgcgtcta actcgtcggt catcaggaaa agtatccgcg tggacaggtc   1020
caagtgagga tttcaggcca atttggtcgc ggcgagcgca atttcaacgc ctccgctgtc   1080
agcctggaag ctcggcctaa ggagcgctca catgcacatc gaaatcggac tgcccagcca   1140
tatcgcccac gtgcggggc ggctgaccgt cgagtgggcc cgccgggccg aacaccgcgg   1200
cttcgccggc ctgccgcga tcgaccggct ggtgtacccg agcctcgacg cgatgaccgc   1260
gctcgcggtg gccgcgggcg cgaccaccgg catcgggttg acgttcaacg tgctgctcgc   1320
tccgctgtac cccgcggtgc tgctggccaa gcaggtcatc accctcgcgg aggcgtccgg   1380
cggccggctg cgcctggggc tgggcgtcgg gagccgctgc gacgactaca ccgccgtcgg   1440
cgtcgactat cggcggcgcg ggcgcattct cgacgagacg cgggcgctgc tgcgtgccgc   1500
gtgtgaggcc gaggtggtga ccggcgacca gccgctgtgc ccggcgccgg tgcggatccc   1560
gatcctgttc ggtggacggg cggacgcgac gatccgccgc gccgtgaccg tcggtgacgg   1620
ctggaccgcc ggggcgctgc gcgattacgc caaccagtcg gtgttcgccg agcgggtccg   1680
ggcggcatgg gcgcgcgggg gccgctccgg acggccgtgg ctgcaggcca gcgtcaactt   1740
cgccttcggc gatgacgagg ccgtcgccgc tggccgcaga cacctgcaga gctactacgg   1800
cttcaagccc gactacgccg ccctcaacgt cgccgacatg ctcaccacgc cgcaggaggc   1860
ggc                                                                 1863

<210> SEQ ID NO 2
<211> LENGTH: 1551
<212> TYPE: DNA
<213> ORGANISM: Mycobacterium avium

<400> SEQUENCE: 2
cccgcaccgc cggtcctgcc gccggacaat gccgcgttgg cttcgccggc tgccgccgtg     60
acgcggcctt cggcggcgac ttcggcgtcc gcggcggcca gcacctcggc ttcacctgcc    120
atggccgcgg ggcccatgtt gcgcatcgcc gtgctggctg tggtggcctg ggtctcgacg    180
ctgaacagct tgtccttcaa catgcccaga cccgtcccga tcggtgacag gatcgtcgag    240
gcgatgttgt agcccttgat cgccaaccat gccgtgccca ttgcacccac accgacggtc    300
accgcatcca gcaacggctt gtgctcggtg agccaatgcg ccgactcccc aagcacccca    360
acgacttcag tcatcgctgg cagaaagtcc tggccgatct cgatgcgggc tgcgctcaac    420 gccccttga agtccttcat cttggcgttg taggtctcct gggattcggt gaatcccttg    480
gtattgcccg caccgtcggc ctgcgcctga ctgacctcct tgaccgcggc agcggctttg    540
ggcccgttct ccccgaccaa ctgcaatacc gtccgcagat tgtcttggcc gccgaccatg    600
agggccagcg cttggatcat cgactggaca tcacccttgc cggacttgag ctgattgttg    660
aagcctgtca atgcttttc ttggttccac cactgctcga caaggttggc ttcctcaacg    720
ctcaagccgc cgcggtcctt gcggaactgc ttgtacgcct cagcattgtt ctggatcgcc    780
gtcgcgaccg cctgcgcctg cgcgggcagc ttcgagaaca tctcattagc gctgtcggcc    840
acctgcttgc tcttgaacca ggcgtccagc gtgaccatcc ccgacgggcc aagcttcgac    900
tggatcgtgt catacaacag gttcgcggtg ccgatcaggc cgcgctcccc gaaatgctcc    960
```

| | |
|---|---|
| tgaatgtcac gggcatccaa accgagctgt cccatctcct gggacatttg ctgggttggc | 1020 |
| ttggccagcg acgtgatcgc gtgcgtcata ttctgggtgg cctgatcagc acccataccc | 1080 |
| gactgagtga gcatcgccaa cgacgcatac aggtcattga cgctttcacc aactccggcc | 1140 |
| gcgaccggct cgacgttgtg caacgccccc gcgaagtctt gcagcgaaac cttcgacaac | 1200 |
| cccacggcca cattcaattt cgaggtgacg ttggcggcct gctcgaccgg gatgtggtag | 1260 |
| tcgtgcatcg tggtcgtgac cgcgctgatc gtctcgccca ggtccgcgcc ctcttcggac | 1320 |
| gcaagctgcg ctgaagccgt caacaccttg atcgcatcac tgccccgata gccggccttc | 1380 |
| tcgacaccca gcgcagcgtc catcagcttt tgaggcgcat aaccgaccac gctcgacagt | 1440 |
| ttcagcacgc catcgctgat cgccttcaga ttggccggcg actcctcggc caccgtgtgc | 1500 |
| agcctctgca cgactgctg gaaattcccc gccgcatcag tcgccgagac a | 1551 |

<210> SEQ ID NO 3
<211> LENGTH: 1847
<212> TYPE: DNA
<213> ORGANISM: Mycobacterium avium

<400> SEQUENCE: 3

| | |
|---|---|
| acatcgggtg gagtgcgggg agatcgagca cgcgctgcgc ggccacccgc tggtcgccgc | 60 |
| cgcgacggtg gtccccatcc acaactgcac tgcgctgggc gccgggatcg tcgtaaccgg | 120 |
| cagcggcgca gagcaatttg acgactccac acccggcgcg ctgcgcgccc atctcgccgt | 180 |
| ccgactcccg cagtacatga tccccaaggt gttcgtctca tgccccgagc taccgctcac | 240 |
| cgccaacggc aaggtcgacc gggcaaaat cgcggcgcgc ctcgaagcgg ccgcgcgggc | 300 |
| accccagccg ctcgacacgt catccaccct cactgtggtc gagcggctgg tcgccgaggt | 360 |
| ctggtccgat gtgctgggcg cgccgatcac cggccgcgag acaatttct tcgcccaggg | 420 |
| cggcgatagc ctgcgcgcca ccgaagcggt cgcccgactg acgcgcaggg gagtggccgg | 480 |
| agcggaggtg ggccagctgc tcagccacca gacgcttggg cagttcagcg cggcgtgtgt | 540 |
| gctcgccgac ccggcatccg aggcatccga gtcggcggcc gatgtcggcg aacccgtgac | 600 |
| accgggcgag gggttcccgc tcacccggtt gcagcaggcc tacacgctgg gcgcggccgg | 660 |
| actcaatggg agcacctgtg caccaacgta tttcgcggtg gtgctggccg ccgcgcccga | 720 |
| gtctgccggt atagacctgg atcggtttgc ccgtgtggtc accagatgcg tcgacgaatt | 780 |
| cgcgatgctg cggtgcgcgc tggacgccga caccacccaa cgggtgcagg tcgacgccgg | 840 |
| gccggtgccc gtccatgacc ttgatataca agacgacccc gacctgttac tgcggcgcat | 900 |
| ggcggccgcc ccgttcgatc cgcattcggt tccggtgatc cagtgcttcg caccgtcgag | 960 |
| gtcaccccgt cacgtcggtc tgctgatcag ctatctgggc ctcgatgccc gcagcctgtc | 1020 |
| caccgtcgtc accacgatca tcgccgaata ccagtcgcaa ccccggccgc ggcaggtcga | 1080 |
| cccgaccgcg gcggtcttcg cccggtttgc ctccgaaagc gcttggggcg aaaacgatgt | 1140 |
| cgacaacagc gttgccggcc ctcgctgct gccgctgcac gaccagcgac gtgacccctt | 1200 |
| cgagcgggtc accttcgcgc ggcgcagctt caccatcgaa gaacaggctg ccgccacgct | 1260 |
| gcgtgagcac gccgcacacc tcggcgtcac ccccaccgcg ctggtcttcg aagccttcgc | 1320 |
| acatgcgctg gcgtcgatcg gcgccggtca gcgattcgcg gtgacagtcc ccaagtcgta | 1380 |
| ccgtcccgac tacgccccg cggaccgcga ggtgttgggc aacttcaccc gcctggcgct | 1440 |
| gtgcgaggtc gactacggcg ccgtgagacc gggatctgcc gaagcggttg ccgcggcgca | 1500 |
| gcgggaactg tggcgcgcgg tgagccacga cggtgacatc accggcgggc tggccgcaac | 1560 |

```
gcggaccgcg ggtggctacc ccgtggtgtt caccagcacc ctggggctca cccatcagga    1620
cgccagcggg ctgaccaacg tgcggacatt gacccagacc ccgggcgtct ggctggactg    1680
ccagaccgag gacgaggtcg ccggaattcg tatgagctgg gacatagcta ccaatgtggt    1740
tgccgcggaa tcgatctcgg tggcttttc ccgattcgag gaggcggtgc ggcgccacgc    1800
ggggcaagcc gagccgccgg gcacggccgt tgctccggcg gtgggcg                  1847
```

<210> SEQ ID NO 4
<211> LENGTH: 4716
<212> TYPE: DNA
<213> ORGANISM: Mycobacterium avium

<400> SEQUENCE: 4

```
agtgggcgag cgcggtgatc gccgccgcgc tgcgccactg ccgacccgag caggtgctgc      60
cgcaatacac catgctggtg cggcgctggg aggcactgcg atacgtcccc tcaggatacg     120
ccgcttccga cgtcgaacgg gcggctcgcc ggttggccgg catcgtcacc ggagccgtgt     180
caccccagac gctgatcgga gacccgcagc tgacgcccga ggcgctgctg ctgcgtgacg     240
accgcatgcg gatggccctc gacgacctgg ccggggccat cttcgggcac gcgcgcacgc     300 tgggcggcg gcttcgcgtc gtggaagtcg gctcccggac cggcctgatc accgaacggt     360
tgaccgagct ggtgggcgtg gtggtcgagg aatacttgtg cctggagcca aacccgacgc     420
tcgccggaat cgccgccggg cggcgcttcc cggccccgac ccgccacgtc gacgcacccg     480
acgcggcgtc gggcgtcgac gtggtgatct gctgtgggtc gctgcatcag ctgcccgacg     540
cggaggcggt cctcgaggcg atcaccgtgt ccgacgacgg ttggctgtgg atggtggaga     600
attccgaggc cacccaagcg acgctcatca gcgcggccgt tctcgacccc ggcctgctcg     660
cgtccgattc gaagacgctg cgtccggccg atcggtggtg gcggctcatc gccgaccacg     720
gttggcgacc gacgcacatg atccaggacg gacccggcct cacgctcatc gcgcaccgcc     780
ccgacaagcc cggcatgccg acaccgccgg ccgaacagcg ccgcgacggt aggtggtcgc     840
gaccggctgt gccggcgtcg tgctgccga ccgacgccac ggtggtggcc acgcttgccg     900
agatctggca gcgtcatctc gccattccaa cacccggcgt cgacgacgac ttcttcctgc     960
tcggcggtga cagcctcgtc gcgacccggg tctacgccga ccttcgggcc gccggttcg    1020 gccaactcgc tttcgtcgac ctgttcaacc actcgacgct cggtgagctc gcggcacacg    1080
ccggcccgcg caccggcccg gaagtgtcgg tggcggctga tcgacccgg ggcggcaccc    1140 acgacccgaa ccgattcccg ctcaccgtcg tgcagaacgc gtatcgggcc gggcgagaag    1200
gcgcgttgat cctcggcggc gtcgccgcgc actgctactt cgagttcgag ctcgcggact    1260
tcgaccggcc gagattcgat tcggccgcac gccaactcgt agcacgccac gccggactgc    1320
gcaccacggt gtcaccggcg ggcaccgacg cggcctcctc gggtgaggtc gccgtcgtgc    1380
acaccgcgcc gatcgagccc gtcgtgcgag accacgacga cgtgcgagcc gcgatgcgcg    1440
accagatcat cgacttgacg gcccgcccgg gcatcgactt cggggtgcaa acccgcggcg    1500
acgggcgcac cgtcgtcggc atcagcatgg acaacaccat gctcgacggc gccagcatga    1560
tgatcgccct gtccgaactc gatcacctct atcgcggcga aaccgttgac caattgccgc    1620
cgctggaaac gtcttcgcg cactacgtgt ggaaccaccc ggagctgctg cccgacgccg    1680
acgaggcggt gctgccgcgg ctggccgcca ccgagacta ttggcgcgca cgcctgccat    1740 cttgccgcc ggcgccgaaa ttggccgaca tgtcactgct gttcgagatc gaggagccga    1800
```

```
ggttcgaacg ggcaaccgcg accattcccg ccgtcgactg gtcgcaggta acgcgatcgt    1860
gccgtgccga gggcgtcacc gtcgcgtcat ttctgctcgc caactatgca cgggtgctgt    1920
ctcggtggtc ggggaccgac cacttctgca tcaacgtcac gctattcgac cgcgaccccg    1980
atgtcgtggg gatcgaaaac gtcgtcggag atttcacttc cctggtgttg ttggagtgcc    2040
gagtcgatga gcccgcctcg atctgggaga gcgtgcgcgc tctgcagcgg caattgatga    2100
ccgacctgcc gcaccgcggc gcggacgcgg tgtggctgca acgcgaactg ctgcggtttc    2160
acggcaaccc gacggccgcg ctgttcccg tcgtcttcac cagcggactg ggccttgtcg     2220
acgcctcggc tcgggcggcg gtccggttcg ccgaaccggt attcgccgcc tcgcagacac    2280
cgcagacggt gttggacttc caggtgtggg aaagcgcggg ggcgctgaag ctgtcgtggg    2340
acttcgtcag tcaggcggtg tcgccggcca ccgcgcgcac tcagctcgag tcgttggtgg    2400
acggcatcac cggtgtcgcc acacgcagcc gccgcatcga acacaagttg ggcgagggg     2460
catccaatga cgagctcctg caacgtgttt cgaggatctg cgcgtccgcc ctgggtcagc    2520
cgagggtcga acctcacgac aatttcttcc agctcggcgg cgattcggtc agcgcgacca    2580
aggtggtcga acagatcggc cgtgagctgt cagcctcggc caccttcga ctgctgttcg     2640
ccaatccggt gatcggcgac ttcgccgcca aaatcgccga cactgacaac gccgacgaac    2700
ccgacctgac cgttgaggag ggcatgttat gaccgcggcc gagctcgtcg accacctgcg    2760
gggtatcggc gtccaactgt gggccgacgg tgagaatttg cgctaccgag caccgcaaca    2820
agtcctcacc gcggacctga aagctcaact ggcggcggtc aaaacggacg tgattaccct    2880
gctggcggaa gagacgaccc tgctgcgcgc gccgcaggac cggttcgagc cgtttccgct    2940
caccgacgtg caagccgcat atctggtcgg gcgcacgtcg gcgtttcagt ggggcggggt    3000
aggctgccac ggctacgccg agttcgcggt cgaccacacc gtggcaacac cgagcgccga    3060
gcaatatcgg gaggcgtggc gcaaggttgc cgaccgccac gacatgttgc gctgcgtcgt    3120
tcatcccgag gggtatcagg tgatatgccc cgacgtgccc gacgacgggc tggtcatcca    3180
tcagtgtcac acggtcgaag acgttgccgg cgtacgtgcc ggggtcacgg aacatctgcg    3240
taaccggata tatccgctgg gcgaagcgcc gatgtatgac ctggtgatca cgatgggccc    3300
tgacgacacc gtggtccatc tgtccgttga cctgctgatc gccgacttcg tcagcatctc    3360
catcctgatg accgactttc agcagtgctt gcttgacccc gaatgcgacc ttgcgcccgt    3420
cgatttcagc ttccgcgact acctgctgaa tctcgctcgc gagcgaagct cggccgccgg    3480
tagtgcccgc cgggaacgcg atctcgccta ctggcgggat cggctcgatc agctgccgtc    3540
accactgtcg ttaccggtgc tgcccgacga ctagacgccg tcagcgtcgc ggacggcacc    3600
gaccttttca cggcgttcga tgcgcctgtc ggccgagcgt ttcgaggtgc tcagccggcg    3660
cgcggcagag cacggagcga ccgtcaacgt cgccatcgtg acggcattca gccgggccat    3720
cgcacgctat ggcgatcgcg accatttcct gctgaccctg acgaccatgg accgccacgc    3780
gttcactccc gccgtcgggc agttggtcgg ggatttcacc ggcaccagcg tgctcgaagt    3840
cgatgtccgc ggacagcgca ccttcgccga actgctgcac ggcgtcggtg atcgtctctt    3900
cgacgacatg gaccattcga ccaccggcgg cgtcaacgtc gcccggctcc tggggcagcg    3960
cgacgacgac cgaggtgagc agacgcccgt cgtgttcacc tcgacactcg gcgccacgac    4020
ccgaatcgac agcggcgcaa catctttgtt gcacccgatt caaggtcgcg gtctgagcca    4080
gactcctcag gtgctgctgg actgtcaggt cgccgaaatc gacggcatgc ttgaggtcaa    4140
ctgggacacc cgcgatcagg ccgtgcccgc cgaggtcctc gaccgcgcgt tcgccgactt    4200
```
ccgccacgcc ctggatctgc tcagcaccga cgcctcggcc tggcaccggc cgctattgcc 4260
ggcccagccc cccgagacca caccggtcga ggggccacgc acacaccatg aaccggcgct 4320
gatccatacc gggttcctgc gcaacgtgct ggtgacaccg gatgccgtcg ccatccgcca 4380
cggtgatcgg gccaccacgt acgccgaatt gctcgctgcc gcgaccgcgg tggccgacac 4440
gctggccgcg acgggggtgc ggccgcgtga ctacgtcggt atccggttgc cgcagggccc 4500
cgcccagatc gcggctctcc tgggcgcatt gctggcccgg gccgcctatg tgccgttgga 4560
cgtcggctgg cccactcacc gcgtcgacca gatcgcggcc caatgctcgc tggcagcgct 4620
gtgcgagccg gacggagagg tggaccggct gcttgccgac ccgcagacct ggtcaccgcg 4680
cgcggcggtg gtgccggagc cccacagcga ggtgct 4716

<210> SEQ ID NO 5
<211> LENGTH: 2392
<212> TYPE: DNA
<213> ORGANISM: Mycobacterium avium

<400> SEQUENCE: 5
ccgactccgg taaccagcaa cccgatctgg gctcggttga tgatttcacc ccaggacgca 60
agggcgctcc aaccctcaaa gtggttcacc tcgggctgat gtggggacaa cacggggccg 120
gcatcggtgg ccttgtcaaa aaccggttcg tgaaaatggt cgtatccaaa gatcaggtcg 180
gcccccatac attcggcttg gatgaccgcg gcacgccagg tccggtagtt cggggtcccg 240
gccggctgga tctgaacacc aacggaggag atcattgccc gccacccggc tgtcgatccc 300
gcgagggttg cagtcggtgg gtgatccagt cgaggatgat tgactgggta tctgccgtgt 360
agcccatgtg cccggtggca aagaaccgcg ccgatttggg ggacccgtgc tcgagcagca 420
ggtagtagtc gctgatcggg aatacggtgt cgtgtagccc gttgatgagc agcgtctcag 480
cgcagggccg gtccaggata ccttggcgta caagggacag cttcggcgcg tagtccaccc 540
attgctcgaa ggtgtcgcgc ccaaatgcat aggcgagggt ctcggccagc tcgaaggggt 600
actcgcctga ttgggcctgc tcgatccact cggcgtcaaa gccatggtcg atgcagccgc 660
cttggctgac cacacaggcg agggagttcc ggtgggtgtg ggcgattttg gccgcccagt 720
agccaccggt actaccaccc caatagccca cacccgccgg gtcgagttcg ggtcgcccgg 780
cgatccactc caacacgggg gtgaacattc gctcggcgtc ctccgaacca gccagcggag 840
catcaccgac cccggggatg tcgatcgcca atgttgcgac gttccgggcg agcacctgat 900
cggtgtgcat gtcttccttg aaggtgtcga tcccgcccga gacgagcaat acaggcagcc 960
ggtccgtcgc cttcgggaca cgcagatggg cgatgatgcg gtcaccctcc ccgggccgcc 1020
cggcgaacgg gatctcgaca cgctcgatgg ggatgtcgaa gtaccgggat gcgcgcagca 1080
acatttcctg cgacttgcgg taggcgctct tcttaccggc cgaattcatc gtcgggtagc 1140
gggccatgcg gtagtagcca taggcgcgca aatagttttc gtgtgccaca ctggtgtcgc 1200
caatctgttc ggcctcttcg gctcgggcct gatagcgtgc ggccacggca ctgaacgcgg 1260
ccgcccaggc gtcgcgatca taggagttca ggccgctcaa cacgccctgc acatcatcgg 1320
cgagcgtgta ctgaaacgga taaattcccg ccgtggccga gaccgccata gcggccatag 1380
ctcggtcacc ggtcgcgtgt gtcgcttcac acggccaagt tatgaccgct cgcggctgca 1440
gatattggag aaaacggaca tctcacgcgt gccgtgggcg agccgcaccg ggaagttctg 1500
tgggagccgc tccagccagt gccaggcatt cgctgatcag gtgggactga tcggcgtaac 1560

```
ccgcctcgat cgctagatcg gcccaccgga ttcggtgatc accggcatgg atcaaatcca    1620
gcagccgctg gaaccggaaa atccggccaa gccgcttggg gccgaagccg accgcggcgt    1680
cgaaccgacg gcgaagctgc cgctcgctca acccaacaga ggaggcgaca tccgaaacag    1740
agcgggccgg gtggacacgc agcatctcga ttgagtgcgc cactggctga tcgaccacgg    1800
gatcgatctt gaccacatac cgcgccagca ccgccgccaa taatgcgacc cgttgccgaa    1860
aagcgttggc ctccagcaca tcctcagcca atcggacgc ggatgtcccg aacaccgagt     1920
caacccggat ctgggtatct cttaactcgc tgacaggatg gcccagcacc gcggcggcag    1980
cacccggtcg taaccgcaga ccgatcatcg caccttcggt gcccgcacat tggtcgtaaa    2040
aggttgtggc cggaccagaa accatgactg cgccctcggc ggtgacgaac agatcgacgc    2100
aaccgtccgg catcacccgc agcgccccac ccgcggtatt cgagcgcacc cagccacagt    2160
ccacatacgg cgcgagcgca cccaaaggtc gacactccaa atacccgacc atcacgctca    2220
cattcagcca ggtcctacgt cgctccgcaa caaattgggc cgcaatcctt cgaagccgcc    2280
cggtcagcgc agactcccag gcggcaatac tcgtgaaccg taaactgcgg cgtagaggaa    2340
atgcccgcca gggcgcaaca cccgcgccac ttcggcgaga aagcgtgaca gg            2392
```

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggtgcgcgg tagga                                                     15

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgacctggtc tgcgtcatc                                                 19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
ccgcgaggac ctgctgacgc                                                20

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcgatccggc gaaacg                                                    16

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gacgagttag acgcacagat tct                                              23

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
acgccctgca gttagctccc cg                                               22

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atcgaccggc tggtgtac                                                    18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcgagcagca cgttgaac                                                    18

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
tcgacgcgat gaccgcgctc g                                                21

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cagacacctg cagagctact ac                                               22

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
agcatgtcgg cgacgtt         17

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic probe

<400> SEQUENCE: 17
caagcccgac tacgccgccc t         21

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
tcgcggtgcc gatcag         16

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gtttggatgc ccgtgacatt c         21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 20
ccgcgctccc cgaaatgctc         20

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
cggcgaaccc gtgaca         16

```
<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cacaggtgct cccattgagt                                              20

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
ccgcgcccag cgtgtaggc                                               19

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcgcagcttc accatcga                                                18

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtgcgaaggc ttcgaagac                                               19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
aacaggctgc cgccacgct                                               19

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gccacgacgg tgacatca                                                18

<210> SEQ ID NO 28
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccagggtgct ggtgaaca                                                    18

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
ccgcgttgcg gccagcccg                                                   19

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggaatcgatc tcggtggctt tt                                               22

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccaccgccgg agcaa                                                       15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
ccgcgtggcg ccgca                                                       15

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gccgcgacgg taggt                                                       15

<210> SEQ ID NO 34
<211> LENGTH: 18
```

-continued

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccagatctcg gcaagcgt                                                    18

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
acgacgccgg cacagcc                                                     17

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cggacggaga ggtggac                                                     17

<210> SEQ ID NO 37
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gggctccggc acca                                                        14

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
ttgccgaccc gcagacctg                                                   19

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggtaaccagc aacccgatct g                                                21

<210> SEQ ID NO 40
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 40
cccgaggtga accactttga                                                    20

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
tcggttgatg atttcacccc aggacgc                                            27

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggcgtcctcc gaacca                                                        16

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcaacattgg cgatcgacat c                                                  21

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
cagcggagca tcaccgaccc cgg                                                23

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggctcgggcc tgatagc                                                       17

<210> SEQ ID NO 46
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 46
gcggcctgaa ctcctatgat c                                              21

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
ccgcgttcag tgccgtggcc                                                20

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcaatactcg tgaaccgtaa actg                                           24

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtggcgcggg tgttg                                                     15

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
ccctggcggg catttcctct acg                                            23
```

COMPOSITIONS AND METHODS FOR DETECTION OF *MYCOBACTERIUM AVIUM* PARATUBERCULOSIS

CROSS-REFERENCE(S) TO RELATED APPLICATION

This application is a divisional of U.S. application Ser. No. 14/978,243 filed Dec. 22, 2015 (now U.S. Pat. No. 9,926,609), which is a continuation of U.S. application Ser. No. 13/785,409 filed Mar. 5, 2013 (now U.S. Pat. No. 9,255,299), which claims the benefit under 35 U.S.C. § 119(e) to U.S. Provisional Application No. 61/619,196 filed Apr. 2, 2012. The entire contents of the aforementioned applications are incorporated herein.

FIELD

The present teachings relate to compositions, methods and kits for specific detection, diagnosis and differentiation of *Mycobacterium avium* subspecies *paratuberculosis* (MAP) for differentially detecting MAP from other non-MAP microorganisms including other *Mycobacterium avium* subspecies (such as *M. avium* subsp. *hominissuis* (MAH), *Mycobacterium avium* subsp. *avium* (MAA), and *Mycobacterium avium* subsp. *silvaticum* (MAS)) in a variety of mammalian host species.

SEQUENCE LISTINGS

The instant application contains a Sequence Listing which has been submitted via EFS and is hereby incorporated by reference in its entirety.

BACKGROUND

*Mycobacterium avium* subsp. *paratuberculosis* (MAP) is a bacterium that causes Johne's Disease (chronic granulomatous enteritis of the small intestine) in livestock. Johne's disease results in decreased milk production, fetal loss, diarrhea and early death resulting in substantial economic loss to the livestock and dairy industry.

There is a need for assays for the rapid, sensitive and specific detection of infectious pathogens for differential identification of MAP from other bacteria and *Mycobacterium avium* subspecies. Such assays are sought for diagnostic identification of animals infected by MAP.

SUMMARY

The present disclosure, in some embodiments, describes compositions, methods and kits for specific and/or differential detection and diagnosis of MAP from other *Mycobacterium avium* subspecies and/or other non-MAP organisms. Differentially detecting MAP microorganisms from non-MAP organisms in a variety of mammalian host species provides elimination of false positives and superior diagnostic tests which may include one-step diagnosis.

In some embodiments, the present disclosure describes nucleic acid target sequences that are unique to MAP and not present in other *Mycobacterium avium* subspecies. These unique nucleic acid sequences comprise regions of MAP genomes including non-coding regions, coding regions, genes, alleles and variants thereof and/or portions and/or fragments and/or complements thereof. In some embodiments, a nucleic acid target sequence unique to MAP comprises the sequence of SEQ ID. NO: 1, SEQ ID. NO: 2, SEQ ID NO: 3, SEQ ID NO: 4 and/or SEQ ID NO: 5, fragments thereof, complementary sequences thereof as well as sequences having from about 80% to about 99% sequence identity to one of these sequences. In some embodiments, fragments comprise fragments having at least 10, at least 20, at least 25, at least 30, at least 40, at least 50, at least 60, at least 70, at least 80, at least 90 or at least 100, contiguous nucleotides, including all values in-between at least 10 and at least 100 contiguous nucleotides (such as 11, 12, . . . 21, 27 . . . 29 etc.), of any of SEQ ID. NO: 1, SEQ ID. NO: 2, SEQ ID NO: 3, SEQ ID NO: 4 and/or SEQ ID NO: 5. Sequences having 80%-99% sequence identity may include nucleic acid sequences that have 80%, 85%, 90%, 91%, 92%, 93%, 94%, 95%, 96%, 97%, 98% and 99% sequence identity to any one of SEQ ID. NO: 1, SEQ ID. NO: 2, SEQ ID NO: 3, SEQ ID NO: 4 and/or SEQ ID NO: 5 and include all values in-between 80% and 99% not explicitly disclosed.

In some embodiments, compositions comprising isolated nucleic acid sequences of SEQ ID. NO: 1, SEQ ID. NO: 2, SEQ ID NO: 3, SEQ ID NO: 4 and/or SEQ ID NO: 5, fragments thereof, complementary sequences thereof as well as sequences having from about 80% to about 99% sequence identity to one of these sequences are described. In some embodiments, isolated nucleic acid fragments comprise fragments having at least 10, at least 20, at least 25, or at least 30 contiguous nucleotides of any of SEQ ID. NO: 1, SEQ ID. NO: 2, SEQ ID NO: 3, SEQ ID NO: 4 and/or SEQ ID NO: 5. Isolated nucleic acids having 80%-99% sequence identity include nucleic acid sequences that have 80%, 85%, 90%, 91%, 92%, 93%, 94%, 95%, 96%, 97%, 98% and 99% sequence identity to any one of SEQ ID. NO: 1, SEQ ID. NO: 2, SEQ ID NO: 3, SEQ ID NO: 4 and/or SEQ ID NO: 5 and include all values in-between 80% and 99% not explicitly disclosed.

Some embodiments describe oligonucleotide primers for use in a nucleic acid amplification method (such as but not limited to PCR) for the detection of target nucleic acid sequences that are unique to MAP. Oligonucleotide primers of the present disclosure comprise at least two primers, having at least a forward primer and at least a reverse primer, that are operable to hybridize to target nucleic acid sequences that are unique to MAP including portions and/or fragments and/or complements thereof and/or sequences having at least about 90% identity, and/or sequences having at least about 80% identity thereto. Some exemplary non-limiting primer sequences of the present disclosure comprise isolated nucleic acid sequences having the nucleotide sequence, of SEQ ID NO: 6, SEQ ID NO: 7, SEQ ID NO: 9, SEQ ID NO: 10, SEQ ID NO: 12, SEQ ID NO: 13, SEQ ID NO: 15, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, complements thereof and sequences having about 90% identity to the foregoing sequences.

In some embodiments, primer sets are described having at least 1 or at least 2 primer sets, wherein each primer set has at least a forward primer and at least a reverse primer, that are operable to hybridize to target nucleic acid sequences that are unique to MAP including portions and/or fragments and/or complements thereof and/or sequences having at least about 90% identity to, and/or sequences having at least about 80% identity thereto. In some embodiments, primer sets may be nested primers. In some embodiments, primer sets or primers may be degenerate primers.

Some embodiments describe oligonucleotide probe sequences for use in detection of target nucleic acid sequences and/or amplified target sequences that are unique to MAP. Oligonucleotide probes of the present disclosure are operable to hybridize to target nucleic acid sequences that are unique to MAP including portions and/or fragments and/or complements thereof and/or sequences having at least about 90% identity, and/or sequences having at least about 80% identity thereto. Some exemplary non-limiting probe sequences of the present disclosure comprise isolated nucleic acid sequences having the nucleotide sequence, of SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, and SEQ ID NO: 50, complements thereof and sequences having about 90% identity to the foregoing sequences.

In some embodiments, isolated nucleic acid sequence compositions of the disclosure, including primers, probes and polynucleotides/oligonucleotides, can further comprise one or more label, such as, but not limited to, a dye, a radioactive isotope, a chemiluminescent label, a fluorescent moiety, a bioluminescent label an enzyme, and combinations thereof.

The present disclosure, in some embodiments, describes methods (assays) utilizing molecular methods such as nucleic acid sequence specific amplification and detection that offer significant improvements in speed, sensitivity and specificity over traditional microbiological methods. Embodiments relate to design and development of molecular detection assays comprising identification of one or more target nucleic acid sequence that is present in a MAP organism to be detected and absent or divergent in organisms not to be detected. Some embodiments further relate to designing primers, including designing degenerate primers, that can bind to and amplify one or more target nucleic acid sequences encoding for a MAP-specific target nucleic acid and/or a complement and/or a fragment thereof, and using the designed primers to amplify and detect such target nucleic acid sequences.

In some embodiments, methods of detecting in a sample the presence of a MAP microorganism are disclosed. In some embodiments, methods of detecting the presence of a MAP strain are described.

The specification also discloses methods for detection of a MAP organism from a sample and methods to exclude the presence of MAP organism in a sample, wherein the detection of at least one nucleic acid sequence that is specific for a MAP organism is indicative of the presence of a MAP organism and the absence of detection of any nucleic acid sequence unique to a MAP organism is indicative of the absence of a MAP organism in the sample.

In some embodiments, methods of detection of MAP comprise detection of one or more target nucleic acid sequences that are unique to MAP including portions and/or fragments and/or complements thereof and/or sequences having at least about 90% identity to, and/or sequences having at least about 80% identity thereto.

Accordingly, a method of the disclosure, in some embodiments, can comprise detecting, in a sample, at least one (or more) nucleic acid sequence(s) having at least 10 to at least 25 contiguous nucleic acids of one (or more) MAP specific nucleic acid targets and/or complementary sequences thereof, wherein detection of at least one nucleic acid sequence indicates the presence of an MAP organism in the sample. Non-limiting examples of MAP specific nucleic acids that can be detected include SEQ ID. NO: 1, SEQ ID. NO: 2, SEQ ID NO: 3, SEQ ID NO: 4 and/or SEQ ID NO: 5, fragments thereof, complementary sequences thereof as well as sequences having from about 80% to about 99% sequence identity to one of these sequences (see also Table 6). Methods of detection can also comprise identification steps and can further comprise steps of sample preparation. Such embodiments are described in detail in sections below.

One embodiment method for detection of a MAP organism from a sample comprises: detecting the presence of an MAP-specific target nucleic acid and/or a fragment or a complement thereof comprising: amplifying an MAP-specific nucleic acid and/or a fragment and/or a complement thereof by contacting nucleic acids present in the sample with at least one primer set, having one forward primer and one reverse primer that can hybridize to and amplify the MAP-specific nucleic acid and/or a fragment and/or a complement thereof, under conditions suitable for amplification, and detecting an amplified nucleic acid, wherein detecting an amplified nucleic acid amplified by the primers confirms the presence of a MAP organism in a sample. In some embodiments, more than one primer can be used to amplify one or more amplification products.

Non-limiting exemplary primer pairs comprise a primer pair such as SEQ ID NO: 6 and SEQ ID NO: 7; or SEQ ID NO: 9 and SEQ ID NO: 10; or SEQ ID NO: 12 and SEQ ID NO: 13; or SEQ ID NO: 15 and SEQ ID NO: 16; or SEQ ID NO: 18 and SEQ ID NO: 19; or SEQ ID NO: 21 and SEQ ID NO: 22; or SEQ ID NO: 24 and SEQ ID NO: 25; or SEQ ID NO: 27 and SEQ ID NO: 28; or SEQ ID NO: 30 and SEQ ID NO: 31; or SEQ ID NO: 33 and SEQ ID NO: 34; or SEQ ID NO: 36 and SEQ ID NO: 37; or SEQ ID NO: 39 and SEQ ID NO: 40; or SEQ ID NO: 42 and SEQ ID NO: 43; or SEQ ID NO: 45 and SEQ ID NO: 46; or SEQ ID NO: 48 and SEQ ID NO: 49; complements thereof and sequences having about 90% identity to the foregoing sequences, wherein one of the two primers of each primer set is a forward primer and the other is a reverse primer.

Accordingly, an example embodiment method for detection of a MAP organism from a sample comprises: detecting the presence of a MAP-specific nucleic acid and/or a fragment and/or a complement thereof comprising: amplifying an MAP-specific nucleic acid and/or a fragment and/or a complement thereof contacting nucleic acids present in the sample with at least one primer set, each primer set having one forward primer and one reverse primer, comprising the at least one primer set selected from: SEQ ID NO: 6 and SEQ ID NO: 7; or SEQ ID NO: 9 and SEQ ID NO: 10; or SEQ ID NO: 12 and SEQ ID NO: 13; or SEQ ID NO: 15 and SEQ ID NO: 16; or SEQ ID NO: 18 and SEQ ID NO: 19; or SEQ ID NO: 21 and SEQ ID NO: 22; or SEQ ID NO: 24 and SEQ ID NO: 25; or SEQ ID NO: 27 and SEQ ID NO: 28; or SEQ ID NO: 30 and SEQ ID NO: 31; or SEQ ID NO: 33 and SEQ ID NO: 34; or SEQ ID NO: 36 and SEQ ID NO: 37; or SEQ ID NO: 39 and SEQ ID NO: 40; or SEQ ID NO: 42 and SEQ ID NO: 43; or SEQ ID NO: 45 and SEQ ID NO: 46; or SEQ ID NO: 48 and SEQ ID NO: 49, wherein the contacting is performed under conditions suitable for an nucleic acid amplification reaction; and detecting an amplified nucleic acid, wherein detecting an amplified nucleic acid using the primers confirms the presence of a MAP organism in a sample.

In one embodiment a method for detection of a MAP organism from a sample comprises: detecting the presence of one or more MAP specific nucleic acids and/or a fragment or a complement thereof comprising: contacting nucleic acids present in a sample with a multiplex of primer sets each primer set having one forward primer and one reverse primer, comprising a first primer set, a second primer set, and optionally a third (a fourth etc.) primer sets, under conditions optimal for an amplification reaction to obtain one or more amplified nucleic acids; and detecting the one or more amplified nucleic acids, wherein detecting an amplified nucleic acid using the primers confirms the presence of a MAP organism in the sample.

Some embodiments describe a method for detection of a MAP organism from a sample comprising: detecting the presence of one or more MAP-specific nucleic acids including detecting a first MAP specific nucleic acid and/or a fragment or a complement thereof comprising: a) amplifying from a sample a first MAP specific nucleic acid and/or a fragment or a complement thereof by contacting nucleic acids present in the sample with at least a first primer set, having one forward primer and one reverse primer, the first primer set designed to amplify the first MAP specific nucleic acid and/or a fragment or a complement thereof; and b) amplifying simultaneously from the same sample a second MAP specific nucleic acid and/or a fragment or a complement thereof by simultaneously contacting nucleic acids present in the sample with at least a second primer set, having one forward primer and one reverse primer, the second primer set designed to amplify the second MAP specific nucleic acid and/or a fragment or a complement thereof, wherein the contacting in steps a) and b) is performed under conditions suitable for a nucleic acid amplification reaction; and detecting at least one amplified nucleic acid amplified by either the amplification reactions of steps a) and/or b), wherein detection of at least one amplified nucleic acid indicates the presence of a MAP organism in the sample. In some embodiments a first and a second amplification product can be detected to indicate the presence of a MAP organism in the sample. Furthermore, the process can be optionally repeated to detect a third, a fourth and additional MAP specific nucleic acid molecules.

In other embodiments, not detecting any amplified product using one or more methods described above can be used to exclude the presence of a MAP organism in a sample.

Amplification reactions can comprise a PCR amplification, an end-point determination, a quantitative amplification, a real-time PCR such as a SYBR® Green Assay or a TaqMan® As say.

Detection can be performed by a variety of methods, such as but not limited to, a nucleic acid amplification reaction such as described in the paragraph above. Detection in some embodiments can be performed by hybridization using probes specific to amplified nucleic acid sequences encoding a MAP specific target nucleic acid sequence. Combinations of amplification and hybridization can be used for detection according to some embodiments. Example probe sequences of the disclosure that can be used for detecting in a method of the present disclosure are SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, and SEQ ID NO: 50, complements thereof and sequences having about 90% identity to the foregoing sequences.

In some embodiments, probes can be used to detect and/or to identify a nucleic acid sequence amplified described in the methods above. For example, a probe comprising SEQ ID NO:8 can be used to detect an amplified nucleic acid amplified by using primer set having SEQ ID NO: 6 and SEQ ID NO 7; a probe having SEQ ID NO:11 can be used to detect an amplified nucleic acid amplified by using primer set having SEQ ID NO: 8 and SEQ ID NO 9; a probe having SEQ ID NO 14 can be used to detect an amplified nucleic acid amplified by using primer set having SEQ ID NO: 12 and SEQ ID NO: 13; a probe comprising SEQ ID NO:17 can be used to detect an amplified nucleic acid amplified by using primer set having SEQ ID NO: 15 and SEQ ID NO 16; a probe having SEQ ID NO:20 can be used to detect an amplified nucleic acid amplified by using primer set having SEQ ID NO: 18 and SEQ ID NO 19; a probe having SEQ ID NO 23 can be used to detect an amplified nucleic acid amplified by using primer set having SEQ ID NO: 21 and SEQ ID NO:22; a probe comprising SEQ ID NO:26 can be used to detect an amplified nucleic acid amplified by using primer set having SEQ ID NO: 24 and SEQ ID NO 25; a probe having SEQ ID NO:29 can be used to detect an amplified nucleic acid amplified by using primer set having SEQ ID NO: 27 and SEQ ID NO 28; a probe having SEQ ID NO 32 can be used to detect an amplified nucleic acid amplified by using primer set having SEQ ID NO: 30 and SEQ ID NO:31; a probe comprising SEQ ID NO:35 can be used to detect an amplified nucleic acid amplified by using primer set having SEQ ID NO: 33 and SEQ ID NO 34; a probe having SEQ ID NO:38 can be used to detect an amplified nucleic acid amplified by using primer set having SEQ ID NO: 36 and SEQ ID NO 37; a probe having SEQ ID NO 41 can be used to detect an amplified nucleic acid amplified by using primer set having SEQ ID NO: 39 and SEQ ID NO:40; a probe comprising SEQ ID NO:44 can be used to detect an amplified nucleic acid amplified by using primer set having SEQ ID NO: 42 and SEQ ID NO 43; a probe having SEQ ID NO:47 can be used to detect an amplified nucleic acid amplified by using primer set having SEQ ID NO: 45 and SEQ ID NO 46; and a probe having SEQ ID NO 50 can be used to detect an amplified nucleic acid amplified by using primer set having SEQ ID NO: 48 and SEQ ID NO:49.

In one embodiment, disclosed is an assay for the detection of a MAP organism in a sample comprising a) hybridizing a first pair (or set) of PCR primers selected from a row in the Table 3 described as forward primers and reverse primers (selected from primer sets described in the paragraph above), and complements thereof to at least a first MAP target polynucleotide sequence and/or fragment thereof; b) amplifying the at least first target MAP polynucleotide sequences; and c) detecting the at least first and the at least second amplified target polynucleotide sequence products; wherein the detection of the at least first amplified target polynucleotide sequence product and the detection of the at least second amplified target polynucleotide sequence product is indicative of the presence of a MAP organism in the sample. The method can also comprise hybridizing a second pair of PCR primers selected from another row in Table 3 described as forward primers and reverse primers, and complements thereof to at least a second target MAP polynucleotide sequence and/or fragment thereof.

In further embodiments, the detection can comprise using hybridization with one or more probes. Probes that can be used are described in Table 3 where different probes specific to different amplified MAP target sequences. Primer-probe combinations are outlined in the Table 3 and also set forth in the sections above (for example, amplification product amplified using primers SEQ ID NO:6 and SEQ ID NO:7 can be detected using probe SEQ ID NO:8).

In some embodiments, hybridization can comprise at least a first probe and a second probe, the first probe further comprising a first label and the second probe further comprising a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and the second probe is labeled with VIC® dye.

In some embodiments, any detection method described above can further comprise preparing a sample for PCR amplification (prior to hybridizing), for example, but not limited to (1) bacterial enrichment, and/or (2) separation of bacterial cells from the sample, and/or (3) cell lysis, and/or (4) nucleic acid extraction. In some embodiments, a detection method can comprise DNA isolation from a sample.

Samples may include without limitation, veterinary samples, animal-derived samples, clinical samples, food/beverage samples, water samples, and environmental sample. Veterinary samples may be derived from animals such as but not limited to all ruminants, cattle, sheep, bison, deer, rabbits, foxes and birds including poultry birds, other domesticated and wild birds.

Methods can include multiplex assays such as polymerase chain reactions, wherein hybridizing and amplifying of the first pair of polynucleotide primers occurs in a first vessel and the hybridizing and amplifying of the second pair of polynucleotide primers occurs in a second vessel, or hybridizing and amplifying of the first pair of polynucleotide primers and the hybridizing and amplifying of the second pair of polynucleotide primers occurs in a single vessel, the detection is a real-time assay, the real-time assay is a SYBR® Green dye assay or a TaqMan® assay. Methods can also comprise using additional primers such as a third primer pair and a fourth primer pair and so on.

A method of the disclosure can further comprise providing a first probe and a second probe (and additional probes such as a third probe and a fourth probe and so on), wherein the first and second probes are different from each other, the first probe operable to identify the first amplified target polynucleotide sequence and the second probe operable to identify the second amplified target nucleotide sequence, the first probe further comprises a first label and the second probe further comprises a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and the second probe is labeled with VIC® dye; and hybridizing the first and second probes to the PCR amplified fragments to detect the presence of the first amplified target polynucleotide sequence and the second amplified target polynucleotide sequence from the sample.

Some embodiments describe kits suitable for identifying the presence of a MAP organism. Such a kit can comprise at least one set of oligonucleotide primers for use in a PCR process for the detection of a MAP target nucleic acid sequence.

A first probe can further comprise a first label and a second probe further comprise a second label, both labels are selected from a dye, a radioactive isotope, a chemiluminescent label, and an enzyme, the dye comprises a fluorescein dye, a rhodamine dye, or a cyanine dye, and the first probe is labeled with FAM™ dye and the second probe is labeled with VIC® dye. Kits can without limitation contain other buffers, molecular bio reagents, and one or more container means for kit components.

In the following description, certain aspects and embodiments will become evident. It should be understood that a given embodiment need not have all aspects and features described herein. It should be understood that these aspects and embodiments are merely exemplary and explanatory and are not restrictive of the invention. It is to be understood that both the foregoing general description and the following detailed description are exemplary and explanatory only and are not restrictive of the invention, as claimed.

DETAILED DESCRIPTION

The present disclosure, in some embodiments, describes compositions, kits and methods for detection of MAP. Some embodiments describe specific detection of MAP from a sample even when non-MAP *Mycobacterium avium* organisms are present in the sample.

MAP is a bacterium that infects livestock and several herd animals and causes Johne's Disease which is characterized by chronic granulomatous enteritis of the small intestine. In livestock especially diary animals such as cows, sheep and bison, Johne's disease results in decreased milk production, fetal loss, diarrhea and early death resulting in substantial economic loss to the livestock industry. Existing assays that are used to detect the presence of MAP in samples obtained from animals and to diagnose Johne's disease are based on the detection of insertion sequences present in MAP. MAP is also believed to be linked to human Crohn's disease.

*Mycobacterium avium* complex (MAC) consists of multiple *Mycobacterium avium* subspecies that can be found as environmental contaminants in soil and water (Covert et al., 1999; Falkinham et al., 2001; Le Dantec et al., 2002; Santos et al., 2005; Hilborn et al., 2008), as well as infectious agents for animals such as pigs, cattle, sheep and birds (C. Cayrou et al 2010). Organisms classified in the MAC complex include *Mycobacterium* subsp. *avium, Mycobacterium avium* subsp *paratuberculosis, Mycobacterium avium* subsp *silvaticum*, and *Mycobacterium* subsp *hominissuis*. Symptoms of infection vary by host species and MAC organism. Common methods used for identifying MAC subspecies include DNA sequencing, particularly of the 16S and rpoB genes, and RFLP (restriction fragment length polymorphism) analysis (C. Cayrou et al 2010).

In some cases, certain nucleic acid insertion sequences have been associated with some *Mycobacterium* subspecies and this has been used to detect these organisms. For example, insertion sequences known as ISMAP02 and IS900 are detected in existing PCR-based MAP detection assays which rely on detecting or determining the presence of the ISMAP02 or IS900 target nucleic acid sequences in a sample.

Next-generation sequencing, using an Ion Torrent Personal Genome Machine (PGM) was performed herein to get complete genome sequences for 16 *Mycobacterium avium* subspecies. Sequences were obtained for one *M. avium* subsp. *silvaticum* sample; four *M. avium* subsp. *avium* samples; two *M. avium* subsp. *hominissuis* samples; three *M. avium* samples with an unknown subtype; and six *M. avium* subsp. *paratuberculosis* samples. The sequenced genomes were analyzed to look for the presence of all previously known insertion sequences as well as for new highly specific single-gene targets. A partial ISMAP02 sequence was found in all organisms indicating that ISMAP02 is not an optimal sequence to use for a MAP-specific assay. Results were also confirmed with qPCR testing using the TaqMan® MAP reagents. Results of this analysis are presented in Table 1.

TABLE 1

| Sample Number | Pathogen | Host | 1:100X Sample Dilution MAP CT 1 | MAP CT 2 | ISMAP02 Sequencing Results |
|---|---|---|---|---|---|
| ATCC 49884 | M. silvaticum | Wood pigeon | Undetermined | Undetermined | parital ISMAP02 sequence (position 1-240) |
| 10-5581 | M. avium subsp. Avium | Asian Elephant | 16.94 | 16.96 | ISMAP02 positive, full sequence |
| 10-9275 | M. avium subsp. Avium | Red Tailed Hawk | Undetermined | Undetermined | parital ISMAP02 sequence (position 1-240) |
| 11-4751 | M. avium subsp. Avium | Ruddy Duck | Undetermined | Undetermined | parital ISMAP02 sequence (position 1-240 and 360-519) |
| 05-4293 | M. avium | Avian broadbill from Dallas Zoo | Undetermined | 37.45 | parital ISMAP02 sequence (position 1-240) |
| 10-4249 | M. avium subsp. hominissuis | White lipped deer | 14.78 | 14.76 | ISMAP02 positive, full sequence |
| 10-5606 | M. avium subsp. hominissuis | Pig | 30.24 | 30.95 | parital ISMAP02 sequence (position 1-240 and 360-519) |
| 10-5560 | Unknown MAC subtype | Pig | 15.49 | 15.48 | ISMAP02 positive, full sequence |
| 09-5983 | Unknown MAC subtype | Dog | 16.43 | 16.43 | ISMAP02 positive, full sequence |
| 11-0986 | Unknown MAC subtype | deer | 16.22 | 16.23 | ISMAP02 positive, full sequence |
| 10-4404 | M. avium subsp. paratuberculosis | bison | 14.38 | 14.40 | ISMAP02 positive, full sequence |
| 10-5975 | M. avium subsp. paratuberculosis | bison | 14.74 | 14.79 | ISMAP02 positive, full sequence |
| 10-5864 | M. avium subsp. paratuberculosis | cattle | 14.44 | 14.45 | SMAP02 positive, full sequence |
| 10-8425 | M. avium subsp. paratuberculosis | cattle | 14.74 | 14.70 | ISMAP02 positive, full sequence |
| 08-8281 | M. avium subsp. paratuberculosis | sheep | 14.82 | 14.82 | ISMAP02 positive, full sequence |
| 11-1786 | M. avium subsp. paratuberculosis | sheep | 14.76 | 14.75 | ISMAP02 positive, full sequence |

Other insertion sequences, including IS901 were also found to be non-specific for MAP. The IS901 sequence was present in the M. avium subsp. silvaticum sequence, and two of the M. avium subsp. avium sequences (isolates 11-4751 and 10-9275).

In one embodiment of the current teachings, bioinformatic and direct DNA sequencing comparisons of several Mycobacterium avium species were conducted to identify MAP-specific target nucleic acids sequences. Alignment of these sequences using custom algorithms identified several MAP-specific target regions to which primer pairs of the disclosure were designed for each identified MAP-specific target region to specifically amplify only the unique MAP-specific target sequences against both inclusion (organism to be detected, i.e., MAP organisms) and exclusion genomes (organisms not to be detected, non-MAP organisms).

Exemplary embodiments of nucleic acid target sequence unique to MAP identified herein include nucleic acids having SEQ ID. NO: 1, SEQ ID. NO: 2, SEQ ID NO: 3, SEQ ID NO: 4 and/or SEQ ID NO: 5, fragments thereof, complementary sequences thereof as well as sequences having from about 80% to about 99% sequence identity to one of these sequences.

Genome coordinates for SEQ ID. NO: 1, SEQ ID. NO: 2, SEQ ID NO: 3, SEQ ID NO: 4 and/or SEQ ID NO:5, are described in Table 2 below in relation to the MAP genome described in GenBank accession number NC_002944. For example, nucleic acid target sequence unique to MAP comprising the sequence of SEQ ID. NO: 1 corresponds to a 1,863 bp nucleic acid sequence starting from position 238,936 and continuing through position 240,798 of the MAP genome described as NC_002944. SEQ ID. NOs: 1-5 are described here and in the Sequence Listing below.

GenBank accession number NC_002944 can be found at http://www.ncbi.nlm.nih.gov/nuccore/nc_002944 referenced as "Mycobacterium avium subsp. paratuberculosis K-10, complete genome" 16 Sep. 2011, (1. Li, L., Bannantine, J. P., Zhang, Q., Amonsin, A., May, B. J., Alt, D., Banerji, N., Kanjilal, S. and Kapur, V. "The complete genome sequence of Mycobacterium avium subspecies paratuberculosis," Proc. Natl. Acad. Sci. U.S.A., 102 (35), 12344-12349 (2005); 2. CONSR™ NCBI Genome Project Direct Submission, Submitted (11 Sep. 2004) National Center for Biotechnology Information, NIH, Bethesda, Md. 20894, USA; 3. Li, L., Bannantine, J., Zhang, Q., Amonsin, A., Alt, D. and Kapur, V., Direct Submission, Submitted (5 Sep. 2003) Biomedical Genomics Center, University of Minnesota, 1971 Commonwealth Ave., St. Paul, Minn. 55108, USA).

TABLE 2

| | MAP genome coordinates (NC_002944) | | | |
|---|---|---|---|---|
| Assay ID Number | Signature left | Signature right | Signature length | SEQ ID. NO: |
| 61801, 61802, 61803, 61805 | 238936 | 240798 | 1863 | SEQ ID. NO: 1 |
| 61808 | 3088062 | 3089612 | 1551 | SEQ ID. NO: 2 |
| 61813, 61815, 61816, 61817 | 4168103 | 4169949 | 1847 | SEQ ID. NO: 3 |
| 61819, 61822 | 4169965 | 4174680 | 4716 | SEQ ID. NO: 4 |
| 61823, 61825, 61826, 61829 | 4194685 | 4197076 | 2392 | SEQ ID. NO: 5 |

In some embodiments, compositions of the disclosure comprise isolated nucleic acids having SEQ ID. NO: 1, SEQ ID. NO: 2, SEQ ID NO: 3, SEQ ID NO: 4 and/or SEQ ID NO: 5, fragments thereof, complementary sequences thereof as well as sequences having from about 80% to about 99% sequence identity to one of these sequences. Sequences having 80%-99% sequence identity include isolated nucleic acid sequences that have 80%, 85%, 90%, 91%, 92%, 93%, 94%, 95%, 96%, 97%, 98% and 99% sequence identity to any one of SEQ ID. NO: 1, SEQ ID. NO: 2, SEQ ID NO: 3, SEQ ID NO: 4 and/or SEQ ID NO: 5 and/or fragments thereof and/or complementary sequences thereof and include all values in-between 80% and 99% not explicitly disclosed. Fragments include oligonucleotides or polynucleotides having at least 10 contiguous nucleotide sequences, or at least 20 contiguous nucleotide sequences, or at least 25 contiguous nucleotide sequences, or at least 30 contiguous nucleotide sequences in any part of SEQ ID. NO: 1, SEQ ID. NO: 2, SEQ ID NO: 3, SEQ ID NO: 4 and/or SEQ ID NO: 5 and/or fragments thereof and/or complementary sequences thereof and sequences having at least 90% identity to the foregoing sequences.

Compositions of the disclosure comprise probe and/or primer sequences that are specific to hybridize to (and amplify in the case of primers or detect in the case of probes) one or more target nucleic acid sequences that are unique to a MAP organism. A target nucleic acid sequence unique to a MAP organism may include a gene, a non-coding region, an allele or a complement thereof that is present in a MAP organism but absent from a non-MAP organism. In some embodiments, a target nucleic acid sequence unique to a MAP organism is absent from other *Mycobacterium avium* subspecies which are otherwise very similar or closely related. Target nucleic acid sequences as described in this disclosure can comprise portions and/or fragments and/or complements thereof and/or sequences having at least about 90% identity to, and/or sequences having at least about 80% identity thereto and/or from about 70% to about 90% identity to a target nucleic acid sequence unique to a MAP organism and can include a gene, a non-coding region, an allele or a complement thereof that is present in a MAP organism but absent from a non-MAP organism. Some example probe and primer sequences are described in Table 3 in sections ahead.

Several programs for designing primers such as Primer3 (Steve Rozen and Helen J. Skaletsky (2000) "Primer3" on the World Wide Web for general users and for biologist programmers as published in: Krawetz S, Misener S (eds) Bioinformatics Methods and Protocols: Methods in Molecular Biology. Humana Press, Totowa, N.J., pp 365-386), Primer Express® software (Applied Biosystems), and OLIGO 7 (Wojciech Rychlik (2007). "OLIGO 7 Primer Analysis Software". *Methods Mol. Biol.* 402: 35-60) and variations thereof can be used for primer designing. Custom algorithms were used in the present disclosure in conjunction with the new uniquely identified targets to arrive at primer and probe compositions described herein. The presently designed PCR primers and probes are useful in assays such as real-time PCR assays to specifically and unambiguously detect MAP organisms with great sensitivity.

In some embodiments, exemplary non-limiting compositions comprising primer sequences of the present disclosure comprise isolated nucleic acid sequences having the nucleotide sequence of SEQ ID NO: 6, SEQ ID NO: 7, SEQ ID NO: 9, SEQ ID NO: 10, SEQ ID NO: 12, SEQ ID NO: 13, SEQ ID NO: 15, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, complements thereof and sequences having about 90% identity to the foregoing sequences.

In some embodiments, primer sets are described having at least 1 or at least 2 primer sets, wherein each primer set has at least a forward primer and at least a reverse primer, that are operable to hybridize to target nucleic acid sequences that are unique to MAP including portions and/or fragments and/or complements thereof and/or sequences having at least about 90% identity to, and/or sequences having at least about 80% identity thereto. In some embodiments, primer sets can be nested primers. In some embodiments, primer sets or primers can be degenerate primers. In some embodiments the present disclosure describes designing multiplex primers that are suitable for multiplex PCR assays.

Some embodiments describe oligonucleotide probe sequences for use in detection of target nucleic acid sequences and/or amplified target sequences that are unique to MAP. Oligonucleotide probes of the present disclosure are operable to hybridize to target nucleic acid sequences that are unique to MAP including portions and/or fragments and/or complements thereof and/or sequences having at least about 90% identity, and/or sequences having at least about 80% identity thereto. Some exemplary non-limiting probe sequences of the present disclosure comprise isolated nucleic acid sequences having the nucleotide sequence, of SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, and SEQ ID NO: 50, complements thereof and sequences having about 90% identity to the foregoing sequences.

Isolated nucleic acid sequence compositions of the disclosure, including primers and probes according to the disclosure, can further comprise one or more label, such as, but not limited to, a dye, a radioactive isotope, a chemiluminescent label, a fluorescent moiety, a bioluminescent label an enzyme, and combinations thereof.

The specification also discloses methods for detection and/or diagnosis of a MAP organism from a sample, wherein the detection of at least one unique or target nucleic acid sequence that is expressed in a MAP organism is indicative of the presence of a MAP organism and the absence of detection of any nucleic acid sequence unique to MAP organism is indicative of the absence of a MAP organism in the sample. Accordingly, some methods of the disclosure exclude the presence of a MAP organism in a sample absent of detection of any nucleic acid sequence unique to MAP organism in the sample. In some embodiments, methods of detecting and/or diagnostically determining in a sample the presence of a MAP microorganisms in the presence of other *Mycobacterium avium* organisms of different subspecies and subtypes are disclosed.

Diagnosis and diagnostic methods of the disclosure can include detecting the presence of a MAP organism to diagnose a MAP organism induced disease or condition. Any animal or human disease or condition caused by a MAP organism is contemplated to be diagnosable by the detection methods disclosed herein that can detect the presence of a MAP organism as defined herein. Non limiting examples include diagnosis of Johne's disease and Crohn's disease.

A method of detection and/or diagnosis of MAP comprises detection of one or more target nucleic acid sequences that are unique to MAP including portions and/or fragments and/or complements thereof and/or sequences having at least about 90% identity to, and/or sequences having at least about 80% identity thereto. Accordingly, a method of the disclosure, in some embodiments, can comprise detecting, in a sample, at least one (or more) nucleic acid sequence(s) having at least 10 to at least 25 nucleic acids of one (or more) MAP specific nucleic acid targets and/or complementary sequences thereof, wherein detection of at least one nucleic acid sequence indicates the presence of an MAP organism in the sample. Non-limiting examples of MAP specific nucleic acids that can be detected include SEQ ID. NO: 1, SEQ ID. NO: 2, SEQ ID NO: 3, SEQ ID NO: 4 and/or SEQ ID NO:5, fragments thereof, complementary sequences thereof as well as sequences having from about 80% to about 99% sequence identity to one of these sequences.

Methods of detection and/or diagnosis of MAP in a sample can also comprise identification steps and can further comprise steps of sample preparation. Preparing a sample for PCR amplification (prior to hybridizing with primers), can, in some embodiments, comprise one or more steps such as, but not limited to (1) bacterial enrichment, and/or (2) separation of bacterial cells from the sample (isolation of DNA from sample), and/or (3) cell lysis, and/or (4) nucleic acid (NA) extraction.

Detection of MAP organisms by the use of methods described herein, in some embodiments, is by an amplification reaction such as a polymerase chain reaction for rapid detection. In general methods of the disclosure include comparing for presence of an MAP organism using suitable controls, for example, typically, an internal positive control can be used in a PCR reaction which will have a detectable signal/positive result and a suitable negative control that will have no detectable signal. Amplification reactions can comprise one or more of the following: a PCR amplification, an end-point determination, a quantitative amplification, a real-time PCR such as a SYBR® Green Assay and/or a Taq-Man® Assay.

Methods can also comprise detecting at least one amplified nucleic acid by hybridization, mass spectrometry, nanostring, microfluidics, chemiluminescence, enzyme technologies and combinations thereof.

In one embodiment, a method for detection of a MAP organism from a sample comprises: detecting the presence of an MAP-specific target nucleic acid and/or a fragment or a complement thereof comprising: amplifying an MAP-specific nucleic acid and/or a fragment and/or a complement thereof by contacting nucleic acids present in the sample with at least one primer set, having one forward primer and one reverse primer that can hybridize to and amplify the MAP-specific nucleic acid and/or a fragment and/or a complement thereof, under conditions suitable for amplification, and detecting an amplified nucleic acid, wherein detecting an amplified nucleic acid amplified by the primers confirms the presence of a MAP organism in a sample.

In some embodiments, more than one primers can be used to amplify one or more amplification products. Non-limiting exemplary primer pairs comprise a primer pair such as SEQ ID NO: 6 and SEQ ID NO: 7; or SEQ ID NO: 9 and SEQ ID NO: 10; or SEQ ID NO: 12 and SEQ ID NO: 13; or SEQ ID NO: 15 and SEQ ID NO: 16; or SEQ ID NO: 18 and SEQ ID NO: 19; or SEQ ID NO: 21 and SEQ ID NO: 22; or SEQ ID NO: 24 and SEQ ID NO: 25; or SEQ ID NO: 27 and SEQ ID NO: 28; or SEQ ID NO: 30 and SEQ ID NO: 31; or SEQ ID NO: 33 and SEQ ID NO: 34; or SEQ ID NO: 36 and SEQ ID NO: 37; or SEQ ID NO: 39 and SEQ ID NO: 40; or SEQ ID NO: 42 and SEQ ID NO: 43; or SEQ ID NO: 45 and SEQ ID NO: 46; or SEQ ID NO: 48 and SEQ ID NO: 49; complements thereof and sequences having about 90% identity to the foregoing sequences, wherein one of the two primers of each primer set is a forward primer and the other is a reverse primer.

One example embodiment method for detection (and/or diagnosis) of a MAP organism from a sample comprises: detecting the presence of a MAP-specific nucleic acid and/or a fragment and/or a complement thereof comprising: amplifying a MAP-specific nucleic acid and/or a fragment and/or a complement thereof contacting nucleic acids present in the sample with at least one primer set, each primer set having one forward primer and one reverse primer, comprising the at least one primer set selected from: SEQ ID NO: 6 and SEQ ID NO: 7; or SEQ ID NO: 9 and SEQ ID NO: 10; or SEQ ID NO: 12 and SEQ ID NO: 13; or SEQ ID NO: 15 and SEQ ID NO: 16; or SEQ ID NO: 18 and SEQ ID NO: 19; or SEQ ID NO: 21 and SEQ ID NO: 22; or SEQ ID NO: 24 and SEQ ID NO: 25; or SEQ ID NO: 27 and SEQ ID NO: 28; or SEQ ID NO: 30 and SEQ ID NO: 31; or SEQ ID NO: 33 and SEQ ID NO: 34; or SEQ ID NO: 36 and SEQ ID NO: 37; or SEQ ID NO: 39 and SEQ ID NO: 40; or SEQ ID NO: 42 and SEQ ID NO: 43; or SEQ ID NO: 45 and SEQ ID NO: 46; or SEQ ID NO: 48 and SEQ ID NO: 49, wherein the contacting is performed under conditions suitable for an nucleic acid amplification reaction; and detecting an amplified nucleic acid, wherein detecting an amplified nucleic acid using the primers confirms the presence of a MAP organism in a sample.

In one embodiment method for detection of a MAP organism from a sample comprises: detecting the presence of one or more MAP specific nucleic acids and/or a fragment or a complement thereof comprising: contacting nucleic acids present in a sample with a multiplex of primer sets each primer set having one forward primer and one reverse primer, comprising a first primer set, a second primer set, and optionally a third (a fourth etc.) primer sets, under conditions optimal for an amplification reaction to obtain one or more amplified nucleic acids; and detecting the one or more amplified nucleic acids, wherein detecting an amplified nucleic acid using the primers confirms the presence of a MAP organism in the sample.

Some embodiments describe a method for detection of a MAP organism from a sample comprising: detecting the presence of one or more MAP-specific nucleic acids including detecting a first MAP specific nucleic acid and/or a fragment or a complement thereof comprising: a) amplifying from a sample a first MAP specific nucleic acid and/or a fragment or a complement thereof by contacting nucleic acids present in the sample with at least a first primer set, having one forward primer and one reverse primer, the first primer set designed to amplify the first MAP specific nucleic acid and/or a fragment or a complement thereof; and b) amplifying simultaneously from the same sample a second MAP specific nucleic acid and/or a fragment or a complement thereof by simultaneously contacting nucleic acids present in the sample with at least a second primer set, having one forward primer and one reverse primer, the second primer set designed to amplify the second MAP specific nucleic acid and/or a fragment or a complement thereof, wherein the contacting in steps a) and b) is performed under conditions suitable for a nucleic acid amplification reaction; and c) detecting at least one amplified nucleic acid amplified by either the amplification reactions of steps a) and/or b), wherein detection of at least one amplified nucleic acid indicates the presence of a MAP organism in the sample. In some embodiments a first and a second amplification product are detected to indicate the presence of a MAP organism in the sample. Furthermore, the method can be optionally repeated to detect a third, a fourth and additional MAP specific nucleic acid molecules.

In other embodiments, not detecting any amplified product using one or more methods described above can be used to exclude the presence of a MAP organism in a sample.

Methods of the disclosure can also use other detection methods in addition to nucleic acid amplification reactions described in the paragraphs above. Detection in some embodiments can be performed by hybridization using probes specific to MAP specific target nucleic acid sequence. Accordingly, probes specific to detect one or more target MAP nucleic acids can be used in a sample, under conditions to promote sequence specific hybridization, to detect presence of a MAP nucleic acid in the sample. In some embodiments, hybridization comprises suing at least a first probe and a second probe, the first probe further comprising a first label and the second probe further comprising a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and the second probe is labeled with VIC® dye.

In some embodiments, combinations of amplification and hybridization can be used for detection and amplified nucleic acid sequences encoding a MAP specific target nucleic acid sequence can be detected as MAP-specific amplification products using MAP specific probes. Some non-limiting example probe sequences of the disclosure that can be used for detecting in a method of the present disclosure are described in SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, and SEQ ID NO: 50, complements thereof and sequences having about 90% identity to the foregoing sequences.

In one embodiment, a method for the detection of a MAP organism in a sample comprises: a) hybridizing a first pair (or set) of PCR primers selected from a row in the Table 3 described as forward primers and reverse primers (selected from primer sets described in the paragraph above), and complements thereof to at least a first MAP target polynucleotide sequence and/or fragment thereof; b) amplifying the at least first target MAP polynucleotide sequences; and c) detecting the at least first and the at least second amplified target polynucleotide sequence products; wherein the detection of the at least first amplified target polynucleotide sequence product and the detection of the at least second amplified target polynucleotide sequence product is indicative of the presence of a MAP organism in the sample. The method can also comprise hybridizing a second pair of PCR primers selected from another row in Table 3 described as forward primers and reverse primers, and complements thereof to at least a second target MAP polynucleotide sequence and/or fragment thereof.

In further embodiments, the detection can comprise using hybridization with one or more probes. Some example probes are described in Table 3 where different probes specific to different amplified MAP target sequences are described. Primer-probe combinations are also outlined in the Table 3. For example, in some non-limiting embodiments, a probe comprising SEQ ID NO:8 can be used to detect an amplified nucleic acid amplified by using primer set having SEQ ID NO: 6 and SEQ ID NO 7; a probe having SEQ ID NO:11 can be used to detect an amplified nucleic acid amplified by using primer set having SEQ ID NO: 8 and SEQ ID NO 9; a probe having SEQ ID NO 14 can be used to detect an amplified nucleic acid amplified by using primer set having SEQ ID NO: 12 and SEQ ID NO: 13; a probe comprising SEQ ID NO:17 can be used to detect an amplified nucleic acid amplified by using primer set having SEQ ID NO: 15 and SEQ ID NO 16; a probe having SEQ ID NO:20 can be used to detect an amplified nucleic acid amplified by using primer set having SEQ ID NO: 18 and SEQ ID NO 19; a probe having SEQ ID NO 23 can be used to detect an amplified nucleic acid amplified by using primer set having SEQ ID NO: 21 and SEQ ID NO:22; a probe comprising SEQ ID NO:26 can be used to detect an amplified nucleic acid amplified by using primer set having SEQ ID NO: 24 and SEQ ID NO 25; a probe having SEQ ID NO:29 can be used to detect an amplified nucleic acid amplified by using primer set having SEQ ID NO: 27 and SEQ ID NO 28; a probe having SEQ ID NO 32 can be used to detect an amplified nucleic acid amplified by using primer set having SEQ ID NO: 30 and SEQ ID NO:31; a probe comprising SEQ ID NO:35 can be used to detect an amplified nucleic acid amplified by using primer set having SEQ ID NO: 33 and SEQ ID NO 34; a probe having SEQ ID NO:38 can be used to detect an amplified nucleic acid amplified by using primer set having SEQ ID NO: 36 and SEQ ID NO 37; a probe having SEQ ID NO 41 can be used to detect an amplified nucleic acid amplified by using primer set having SEQ ID NO: 39 and SEQ ID NO:40; a probe comprising SEQ ID NO:44 can be used to detect an amplified nucleic acid amplified by using primer set having SEQ ID NO: 42 and SEQ ID NO 43; a probe having SEQ ID NO:47 can be used to detect an amplified nucleic acid amplified by using primer set having SEQ ID NO: 45 and SEQ ID NO 46; and a probe having SEQ ID NO 50 can be used to detect an amplified nucleic acid amplified by using primer set having SEQ ID NO: 48 and SEQ ID NO:49.

In some embodiments of the present methods, one assay alone may not be definitive for detecting a MAP organism due to genomic similarity between the genomic regions of other non-MAP organisms. Yet, when two (or more) assays such as but not limited to the assays shown in Table 3 are used either in parallel or as a multiplex assay, e.g., in a real-time TaqMan® assay, for example, where each probe in each of the two (or more) assays has a different label for distinguishing results on a real-time PCR instrument, e.g., a 7500 Fast Real-Time PCR System (Applied Biosystems), a positive result from such an assay is indicative of the presence of a MAP organism. Such dual or multiplex (more than 2 assay sets) assay approach can be used to detect and distinguish MAP organism. Some embodiments describe detecting at least two (or more) of MAP-specific target nucleic acid target regions as positive identification of a MAP organism.

Methods of the disclosure include multiplex assays such as polymerase chain reactions, wherein hybridizing and amplifying of the first pair of polynucleotide primers occurs in a first vessel and the hybridizing and amplifying of the second pair of polynucleotide primers occurs in a second vessel, or hybridizing and amplifying of the first pair of polynucleotide primers and the hybridizing and amplifying of the second pair of polynucleotide primers occurs in a single vessel, the detection is a real-time assay, the real-time assay is a SYBR® Green dye assay or a TaqMan® assay. Methods also comprise using additional primers such as a third primer pair and a fourth primer pair and so on.

A method of the disclosure can further comprise providing a first probe and a second probe (and additional probes such as a third probe and a fourth probe and so on), wherein the first and second probes are different from each other, the first probe operable to identify the first amplified target polynucleotide sequence and the second probe operable to identify the second amplified target nucleotide sequence, the first probe further comprises a first label and the second probe further comprises a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and the second probe is labeled with VIC® dye; and hybridizing the first and second probes to the PCR amplified fragments to detect the presence of the first amplified target polynucleotide sequence and the second amplified target polynucleotide sequence from the sample.

Compositions and methods of the present disclosure are ideally suited for the preparation of a kit suitable for identifying the presence of a MAP organism, such as for example a diagnostic kit. Such a kit can comprise at least one set of oligonucleotide primers for use in a PCR process for the amplification and detection of a MAP-specific target nucleic acid sequence. Some kits of the disclosure comprise at least two sets of oligonucleotide primers for simultaneous use in a multiplex PCR process for the amplification and detection of MAP-specific target nucleic acid sequences. Kits can additionally comprise one or more reagents such as but are not limited to, buffers, nucleotide triphosphates, DNA polymerases, intercalating dye, primers, probes, salt, and instructions for the use of the kit.

In some embodiments, kit primers can be labeled. A kit comprising multiple pairs of primers can have primer pairs each labeled with different labels that may be detectable separately. Probes comprised in kits of the disclosure can be labeled. If a kit comprises multiple probes each probe can be labeled with a different label to allow detection of different target nucleic acids and/or amplification products that are the targets of each different probe.

An example kit for the detection and/or diagnosis of a MAP organism comprises: at least one pair of forward and reverse PCR primers having primer pairs selected from primer pairs described in Table 3 (i.e., at least one primer set selected from: a first primer set having SEQ ID NO: 6 and SEQ ID NO 7; and/or a second primer set having SEQ ID NO: 9 and SEQ ID NO: 10; and/or a third primer set having SEQ ID NO: 12 and SEQ ID NO:13; and/or a fourth primer set having SEQ ID NO: 15 and SEQ ID NO 16; and/or a fifth primer set having SEQ ID NO: 18 and SEQ ID NO: 19; and/or a sixth primer set having SEQ ID NO: 21 and SEQ ID NO: 22; and/or a seventh primer set having SEQ ID NO: 24 and SEQ ID NO: 25; and/or an eighth primer set having SEQ ID NO: 27 and SEQ ID NO: 28; and/or a ninth primer set having SEQ ID NO: 30 and SEQ ID NO: 31; and/or a tenth primer set having SEQ ID NO: 33 and SEQ ID NO: 34; and/or a eleventh primer set having SEQ ID NO: 36 and SEQ ID NO: 37; and/or a twelfth primer set having SEQ ID NO: 39 and SEQ ID NO: 40; and/or a thirteenth primer set having SEQ ID NO: 42 and SEQ ID NO: 43; and/or a fourteenth primer set having SEQ ID NO: 45 and SEQ ID NO: 46; and/or a fifteenth primer set having SEQ ID NO: 48 and SEQ ID NO: 49, or sequences comprising at least 90% nucleic acid sequence identity thereof, or labeled derivatives thereof). In some embodiments, a kit can also have at least one probe selected from probes described Table 3 (i.e., probe sequences of the disclosure having SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, and SEQ ID NO: 50, complements thereof and sequences having about 90% identity to the foregoing sequences, each probe corresponding to the first primer set, second primer set, the third primer set, etc. as described above, respectively, selected based on which primer set is selected).

Another example and kit for the detection and/or diagnosis of a MAP organism comprise: at least two pairs of forward and reverse PCR primers (two primer pairs) selected from primer pairs described in Table 3; and optionally at least two probes selected from probes described Table 3.

A kit of the disclosure can further comprise one or more components such as but not limited to: at least one enzyme, dNTPs, at least one buffer, at least one salt, at least one control nucleic acid sample, loading solution for preparation of the amplified material for electrophoresis, genomic DNA as a template control, a size marker to insure that materials migrate as anticipated in a separation medium, and an instruction protocol and manual to educate a user and limit error in use. Components of kits can be individually and/or in various combinations comprised in one or a plurality of suitable container means.

It is within the scope of these teachings to provide test kits for use in manual applications or test kits for use with automated sample preparation, reaction set-up, detectors or analyzers. In some embodiments, a kit amplification product may be further analyzed by methods such as but not limited to electrophoresis, hybridization, mass spectrometry, nanostring, microfluidics, chemiluminescence and/or enzyme technologies.

For the purposes of interpreting of this specification, the following definitions may apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the phrase "nucleic acid," "oligonucleotide", and polynucleotide(s)" are interchangeable and not intended to be limiting.

As used herein, the phrase "stringent hybridization conditions" refers to hybridization conditions which can take place under a number of pH, salt and temperature conditions. The pH can vary from 6 to 9, preferably 6.8 to 8.5. The salt concentration can vary from 0.15 M sodium to 0.9 M sodium, and other cations can be used as long as the ionic strength is equivalent to that specified for sodium. The temperature of the hybridization reaction can vary from 30° C. to 80° C., preferably from 45° C. to 70° C. Additionally, other compounds can be added to a hybridization reaction to promote specific hybridization at lower temperatures, such as at or approaching room temperature. Among the compounds contemplated for lowering the temperature requirements is formamide. Thus, a polynucleotide is typically "substantially complementary" to a second polynucleotide if hybridization occurs between the polynucleotide and the second polynucleotide. As used herein, "specific hybridization" refers to hybridization between two polynucleotides under stringent hybridization conditions.

As used herein, the term "polynucleotide" refers to a polymeric form of nucleotides of any length, either ribonucleotides, deoxynucleotides, or peptide nucleic acids (PNA), and includes both double- and single-stranded RNA, DNA, and PNA. A polynucleotide may include nucleotide sequences having different functions, including, for instance, coding regions, and non-coding regions such as regulatory regions. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment. An "oligonucleotide" refers to a polynucleotide of the present invention, typically a primer and/or a probe.

As used herein a "target-specific polynucleotide" refers to a polynucleotide having a target-binding segment that is perfectly or substantially complementary to a target sequence, such that the polynucleotide binds specifically to an intended target without significant binding to non-target sequences under sufficiently stringent hybridization conditions. The target-specific polynucleotide can be e.g., a primer or probe and the subject of hybridization with its complementary target sequence.

The term "target sequence", "target signature sequence" "target nucleic acid", "target" or "target polynucleotide sequence" refers to a nucleic acid present in a MAP organism that is not present in other non-MAP organisms and is unique to MAP. The target sequence can be a polynucleotide sequence that is the subject of hybridization with a complementary polynucleotide, e.g. a primer or probe. The target sequence can be composed of DNA, RNA, an analog thereof, and including combinations thereof. The target sequence may be known or not known, in terms of its actual sequence and its amplification can be desired. The target sequence may or may not be of biological significance. Typically, though not always, it is the significance of the target sequence which is being studied in a particular experiment. As non-limiting examples, target sequences may include regions of genomic DNA, regions of genomic DNA which are believed to contain one or more polymorphic sites, DNA encoding or believed to encode genes or portions of genes of known or unknown function, DNA encoding or believed to encode proteins or portions of proteins of known or unknown function, DNA encoding or believed to encode regulatory regions such as promoter sequences, splicing signals, polyadenylation signals, etc.

As used herein an "amplified target polynucleotide sequence product" refers to the resulting amplicon from an amplification reaction such as a polymerase chain reaction. The resulting amplicon product arises from hybridization of complementary primers to a target polynucleotide sequence under suitable hybridization conditions and the repeating in a cyclic manner the polymerase chain reaction as catalyzed by DNA polymerase for DNA amplification or RNA polymerase for RNA amplification.

As used herein, the "polymerase chain reaction" or PCR is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, The Polymerase Chain Reaction, BirkHauser, Boston, Mass. (1994). Each of the above steps may be conducted at a different temperature, preferably using an automated thermocycler (Applied Biosystems LLC, a division of Life Technologies Corporation, Foster City, Calif.). If desired, RNA samples can be converted to DNA/RNA heteroduplexes or to duplex cDNA by methods known to one of skill in the art.

As used herein, "amplifying" and "amplification" refers to a broad range of techniques for increasing polynucleotide sequences, either linearly or exponentially. Exemplary amplification techniques include, but are not limited to, PCR or any other method employing a primer extension step. Other nonlimiting examples of amplification include, but are not limited to, ligase detection reaction (LDR) and ligase chain reaction (LCR). Amplification methods may comprise thermal-cycling or may be performed isothermally. In various embodiments, the term "amplification product" includes products from any number of cycles of amplification reactions.

In certain embodiments, amplification methods comprise at least one cycle of amplification, for example, but not limited to, the sequential procedures of: hybridizing primers to primer-specific portions of target sequence or amplification products from any number of cycles of an amplification reaction; synthesizing a strand of nucleotides in a template-dependent manner using a polymerase; and denaturing the newly-formed nucleic acid duplex to separate the strands. The cycle may or may not be repeated.

Descriptions of certain amplification techniques can be found, among other places, in H. Ehrlich et al., Science, 252:1643-50 (1991), M. Innis et al., PCR Protocols: A Guide to Methods and Applications, Academic Press, New York, N.Y. (1990), R. Favis et al., Nature Biotechnology 18:561-64 (2000), and H. F. Rabenau et al., Infection 28:97-102 (2000); Sambrook and Russell, Molecular Cloning, Third Edition, Cold Spring Harbor Press (2000) (hereinafter "Sambrook and Russell"), Ausubel et al., Current Protocols in Molecular Biology (1993) including supplements through September 2005, John Wiley & Sons (hereinafter "Ausubel et al.").

The term "label" refers to any moiety which can be attached to a molecule and: (i) provides a detectable signal; (ii) interacts with a second label to modify the detectable signal provided by the second label, e.g. FRET; (iii) stabilizes hybridization, i.e. duplex formation; or (iv) provides a capture moiety, i.e. affinity, antibody/antigen, ionic complexation. Labeling can be accomplished using any one of a large number of known techniques employing known labels, linkages, linking groups, reagents, reaction conditions, and analysis and purification methods. Labels include light-emitting compounds which generate a detectable signal by fluorescence, chemiluminescence, or bioluminescence (Kricka, L. in Nonisotopic DNA Probe Techniques (1992), Academic Press, San Diego, pp. 3-28). Another class of labels are hybridization-stabilizing moieties which serve to enhance, stabilize, or influence hybridization of duplexes, e.g. intercalators, minor-groove binders, and cross-linking functional groups (Blackburn, G. and Gait, M. Eds. "DNA and RNA structure" in Nucleic Acids in Chemistry and Biology, 2.sup.nd Edition, (1996) Oxford University Press, pp. 15-81). Yet another class of labels effect the separation or immobilization of a molecule by specific or non-specific capture, for example biotin, digoxigenin, and other haptens (Andrus, A. "Chemical methods for 5' nonisotopic labeling of PCR probes and primers" (1995) in PCR 2: A Practical Approach, Oxford University Press, Oxford, pp. 39-54).

The terms "annealing" and "hybridization" are used interchangeably and mean the base-pairing interaction of one nucleic acid with another nucleic acid that results in formation of a duplex or other higher-ordered structure. The primary interaction is base specific, i.e. A/T and G/C, by Watson/Crick and Hoogsteen-type hydrogen bonding.

The term "end-point analysis" refers to a method where data collection occurs only when a reaction is substantially complete.

The term "real-time analysis" refers to periodic monitoring during PCR. Certain systems such as the ABI 7700 Sequence Detection System (Applied Biosystems, Foster City, Calif.) conduct monitoring during each thermal cycle at a pre-determined or user-defined point. Real-time analysis of PCR with FRET probes measures fluorescent dye signal changes from cycle-to-cycle, preferably minus any internal control signals.

The term "quenching" refers to a decrease in fluorescence of a first moiety (reporter dye) caused by a second moiety (quencher) regardless of the mechanism.

A "primer," as used herein, is an oligonucleotide that is complementary to a portion of target polynucleotide and, after hybridization to the target polynucleotide, may serve as a starting-point for an amplification reaction and the synthesis of an amplification product. Primers include, but are not limited to, spanning primers. A "primer pair" refers to two primers that can be used together for an amplification reaction. A "PCR primer" refers to a primer in a set of at least two primers that are capable of exponentially amplifying a target nucleic acid sequence in the polymerase chain reaction.

The term "probe" comprises a polynucleotide that comprises a specific portion designed to hybridize in a sequence-specific manner with a complementary region of a specific nucleic acid sequence, e.g., a target nucleic acid sequence. In certain embodiments, the specific portion of the probe may be specific for a particular sequence, or alternatively, may be degenerate, e.g., specific for a set of sequences. In certain embodiments, the probe is labeled. The probe can be an oligonucleotide that is complementary to at least a portion of an amplification product formed using two primers.

The terms "complement" and "complementary" as used herein, refer to the ability of two single stranded polynucleotides (for instance, a primer and a target polynucleotide) to base pair with each other, where an adenine on one strand of a polynucleotide will base pair to a thymine or uracil on a strand of a second polynucleotide and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary.

A "label" refers to a moiety attached (covalently or non-covalently), or capable of being attached, to an oligonucleotide, which provides or is capable of providing information about the oligonucleotide (e.g., descriptive or identifying information about the oligonucleotide) or another polynucleotide with which the labeled oligonucleotide interacts (e.g., hybridizes). Labels can be used to provide a detectable (and optionally quantifiable) signal. Labels can also be used to attach an oligonucleotide to a surface.

A "fluorophore" is a moiety that can emit light of a particular wavelength following absorbance of light of shorter wavelength. The wavelength of the light emitted by a particular fluorophore is characteristic of that fluorophore. Thus, a particular fluorophore can be detected by detecting light of an appropriate wavelength following excitation of the fluorophore with light of shorter wavelength.

The term "quencher" as used herein refers to a moiety that absorbs energy emitted from a fluorophore, or otherwise interferes with the ability of the fluorescent dye to emit light. A quencher can re-emit the energy absorbed from a fluorophore in a signal characteristic for that quencher, and thus a quencher can also act as a fluorophore (a fluorescent quencher). This phenomenon is generally known as fluorescent resonance energy transfer (FRET). Alternatively, a quencher can dissipate the energy absorbed from a fluorophore as heat (a non-fluorescent quencher).

As used herein the term "sample" refers to a starting material suspected of harboring a particular microorganism or group of microorganisms. A "contaminated sample" refers to a sample harboring a pathogenic microbe (such as MAP) thereby comprising nucleic acid material from the pathogenic microbe. Examples of samples include, but are not limited to, veterinary samples (samples obtained from animals suspected of harboring or being infected by a microorganism—these may include any body fluid or tissue sample), food samples (including but not limited to samples from food intended for human or animal consumption such as processed foods, raw food material, produce (e.g., fruit and vegetables), legumes, meats (from livestock animals and/or game animals), fish, sea food, nuts, beverages, drinks, fermentation broths, and/or a selectively enriched food matrix comprising any of the above listed foods), water samples, environmental samples (e.g., soil samples, dirt samples, garbage samples, sewage samples, industrial effluent samples, air samples, or water samples from a variety of water bodies such as lakes, rivers, ponds etc., samples obtained from animal pens/barns/farms), air samples (from the environment or from a room or a building), forensic samples, agricultural samples, pharmaceutical samples, biopharmaceutical samples, samples from food processing and manufacturing surfaces, and/or biological samples. A "biological sample" refers to a sample obtained from eukaryotic or prokaryotic sources. Examples of eukaryotic sources include mammals, such as a human, a ruminant a cow, a bison, a sheep, a horse, a pig, a chicken, a turkey, a livestock animal, a fish, a crab, a crustacean, a rabbit, a game animal, a murine animal such as rat or mouse, etc. A biological sample may include tissue samples, cell samples, blood, serum, plasma, pus, cerebrospinal fluid, bone marrow, urine, feces, saliva, milk, mucus, or other materials from a human or a livestock animal. A biological sample can be, for instance, in the form of a single cell, plurality of cells, in the form of a tissue, or in the form of a fluid.

A sample may be tested directly, or may be prepared or processed in some manner prior to testing. For example, a sample may be processed to enrich any contaminating microbe and may be further processed to separate and/or lyse microbial cells contained therein. Lysed microbial cells from a sample may be additionally processed or prepares to separate, isolate and/or extract genetic material from the microbe for analysis to detect and/or identify the contaminating microbe. Analysis of a sample may include one or more molecular methods. For example, according to some exemplary embodiments of the present disclosure, a sample may be subject to nucleic acid amplification (for example by PCR) using appropriate oligonucleotide primers that are specific to one or more microbe nucleic acid sequences that the sample is suspected of being contaminated with. Amplification products may then be further subject to testing with specific probes (or reporter probes) to allow detection of microbial nucleic acid sequences that have been amplified from the sample. In some embodiments, if a microbial nucleic acid sequence is amplified from a sample, further analysis may be performed on the amplification product to further identify, quantify and analyze the detected microbe (determine parameters such as but not limited to the microbial strain, pathogenicity, quantity etc.).

As used herein "preparing" or "preparing a sample" or "processing" or processing a sample" refers to one or more of the following steps to achieve extraction and separation of a nucleic acid from a sample: (1) bacterial enrichment, (2) separation of bacterial cells from the sample, (3) cell lysis, and (4) nucleic acid extraction and/or purification (e.g., DNA extraction, total DNA extraction, genomic DNA extraction, RNA extraction). Embodiments of the nucleic acid extracted include, but are not limited to, DNA, RNA, mRNA and miRNA.

As used herein, "presence" refers to the existence (and therefore to the detection) of a reaction, a product of a method or a process (including but not limited to, an amplification product resulting from an amplification reaction), or to the "presence" and "detection" of an organism such as a pathogenic organism or a particular strain or species of an organism.

As used herein, "detecting" or "detection" refers to the disclosure or revelation of the presence or absence in a sample of a target polynucleotide sequence or amplified target polynucleotide sequence product. The detecting can be by end point, real-time, enzymatic, and by resolving the amplification product on a gel and determining whether the expected amplification product is present, or other methods known to one of skill in the art.

The presence or absence of an amplified product can be determined or its amount measured. Detecting an amplified product can be conducted by standard methods well known in the art and used routinely. The detecting may occur, for instance, after multiple amplification cycles have been run (typically referred to an end-point analysis), or during each amplification cycle (typically referred to as real-time). Detecting an amplification product after multiple amplification cycles have been run is easily accomplished by, for instance, resolving the amplification product on a gel and determining whether the expected amplification product is present. In order to facilitate real-time detection or quantification of the amplification products, one or more of the primers and/or probes used in the amplification reaction can be labeled, and various formats are available for generating a detectable signal that indicates an amplification product is present. For example, a convenient label is typically a label that is fluorescent, which may be used in various formats including, but are not limited to, the use of donor fluorophore labels, acceptor fluorophore labels, flourophores, quenchers, and combinations thereof. Assays using these various formats may include the use of one or more primers that are labeled (for instance, scorpions primers, amplifluor primers), one or more probes that are labeled (for instance, adjacent probes, TaqMan® probes, light-up probes, molecular beacons), or a combination thereof. The skilled person will understand that in addition to these known formats, new types of formats are routinely disclosed. The present invention is not limited by the type of method or the types of probes and/or primers used to detect an amplified product. Using appropriate labels (for example, different fluorophores) it is possible to combine (multiplex) the results of several different primer pairs (and, optionally, probes if they are present) in a single reaction. As an alternative to detection using a labeled primer and/or probe, an amplification product can be detected using a polynucleotide binding dye such as a fluorescent DNA binding dye. Examples include, for instance, SYBR® Green dye or SYBR® Gold dye (Molecular Probes). Upon interaction with the double-stranded amplification product, such polynucleotide binding dyes emit a fluorescence signal after excitation with light at a suitable wavelength. A polynucleotide binding dye such as a polynucleotide intercalating dye also can be used.

As used herein a "MAP organism" or "MAP microorganism" refers to an organism of the subspecies *Mycobacterium avium* subspecies *paratuberculosis* (MAP).

As used herein, a "non-MAP organism" is an organism of the *Mycobacterium avium* Complex (MAC) with the exception of *Mycobacterium avium* subsp. *paratuberculosis*. Non-MAP organisms include *Mycobacterium avium* subspecies *avium* (MAA), *Mycobacterium avium* subsp. *hominissuis* (MAH) and *Mycobacterium avium* subsp. *silvaticum* (MAS), as well as MAC organisms of indeterminate subspecies.

As used herein, a "MAP-specific polynucleotide" refers to a nucleic acid sequence that is able to specifically hybridize to a MAP specific target nucleic acid sequence and/or to a portion and/or complement thereof, under suitable hybridization conditions and which does not hybridize with other nucleic acid sequences that do not encode for a MAP-specific nucleic acid sequence, portions thereof or complements thereof. In some embodiments, a "MAP-specific polynucleotide" of the disclosure may be a probe or primer sequence specific to MAP. It is well within the ability of one skilled in the art, using the present teachings, to determine suitable hybridization conditions based on probe length, G+C content, and the degree of stringency required for a particular application.

It is expected that minor sequence variations in MAP-specific target nucleotide sequences associated with nucleotide additions, deletions and mutations, whether naturally occurring or introduced in vitro, would not interfere with the usefulness of primer and probe sequences disclosed herein in the detection of MAP organisms, as would be understood by one of skill in the art. Therefore, the scope of the present invention as claimed is intended to encompass minor variations in the sequences of the MAP specific target nucleic acid sequences described here and the MAP specific nucleotides, such as, exemplary primer sets and probe sequences set forth here, and all sequences disclosed also comprise sequences having at least a 90% sequence homology to these sequences.

A probe may be RNA or DNA. Depending on the detection means employed, the probe may be unlabeled, radiolabeled, chemiluminescent labeled, enzyme labeled, or labeled with a dye. The probe may be hybridized with a sample in solution or immobilized on a solid support such as nitrocellulose, a microarray or a nylon membrane, or the probe may be immobilized on a solid support, such as a silicon chip or a microarray.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, may depend upon, for example, the nature of the nucleotide sequence, temperature, and buffer conditions. These conditions may also depend on what event is desired, such as hybridization, cleavage, or strand extension. An "isolated" polynucleotide refers to a polynucleotide that has been removed from its natural environment. A "purified" polynucleotide is one that is at least about 60% free, preferably at least about 75% free, and most preferably at least about 90% free from other components with which they are naturally associated.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims. Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.). The term "and/or" means one or all of the listed elements or a combination of any two or more of the listed elements.

There are many known methods of amplifying nucleic acid sequences including e.g., PCR. See, e.g., PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. Nos. 4,683,202, 4,683,195, 4,800,159 4,965,188 and 5,333,675 each of which is incorporated herein by reference in their entireties for all purposes.

Nucleic acid amplification techniques are traditionally classified according to the temperature requirements of the amplification process. Isothermal amplifications are conducted at a constant temperature, in contrast to amplifications that require cycling between high and low temperatures. Examples of isothermal amplification techniques are: Strand Displacement Amplification (SDA; Walker et al., 1992, Proc. Natl. Acad. Sci. USA 89:392 396; Walker et al., 1992, Nuc. Acids. Res. 20:1691 1696; and EP 0 497 272, all of which are incorporated herein by reference), self-sustained sequence replication (3SR; Guatelli et al., 1990, Proc. Natl. Acad. Sci. USA 87:1874 1878), the Qβ replicase system (Lizardi et al., 1988, BioTechnology 6:1197 1202), and the techniques disclosed in WO 90/10064 and WO 91/03573.

Examples of techniques that require temperature cycling are: polymerase chain reaction (PCR; Saiki et al., 1985, Science 230:1350 1354), ligase chain reaction (LCR; Wu et al., 1989, Genomics 4:560 569; Barringer et al., 1990, Gene 89:117 122; Barany, 1991, Proc. Natl. Acad. Sci. USA 88:189 193), transcription-based amplification (Kwoh et al., 1989, Proc. Natl. Acad. Sci. USA 86:1173 1177) and restriction amplification (U.S. Pat. No. 5,102,784).

Other exemplary techniques include Nucleic Acid Sequence-Based Amplification ("NASBA"; see U.S. Pat. No. 5,130,238), Qβ replicase system (see Lizardi et al., BioTechnology 6:1197 (1988)), and Rolling Circle Amplification (see Lizardi et al., Nat Genet 19:225 232 (1998)). The amplification primers of the present invention may be used to carry out, for example, but not limited to, PCR, SDA or tSDA. Any of the amplification techniques and methods disclosed herein can be used to practice the claimed invention as would be understood by one of ordinary skill in the art.

PCR is an extremely powerful technique for amplifying specific polynucleotide sequences, including genomic DNA, single-stranded cDNA, and mRNA among others. Various methods of conducting PCR amplification and primer design and construction for PCR amplification will be known to those of skill in the art. Generally, in PCR a double-stranded DNA to be amplified is denatured by heating the sample. New DNA synthesis is then primed by hybridizing primers to the target sequence in the presence of DNA polymerase and excess dNTPs. In subsequent cycles, the primers hybridize to the newly synthesized DNA to produce discreet products with the primer sequences at either end. The products accumulate exponentially with each successive round of amplification.

The DNA polymerase used in PCR is often a thermostable polymerase. This allows the enzyme to continue functioning after repeated cycles of heating necessary to denature the double-stranded DNA. Polymerases that are useful for PCR include, for example, Taq DNA polymerase, Tth DNA polymerase, Tfl DNA polymerase, Tma DNA polymerase, Tli DNA polymerase, and Pfu DNA polymerase. There are many commercially available modified forms of these enzymes including: AmpliTaq® and AmpliTaq Gold® both available from Applied Biosystems. Many are available with or without a 3- to 5' proofreading exonuclease activity. See, for example, Vent® and Vent®. (exo-) available from New England Biolabs.

Other suitable amplification methods include the ligase chain reaction (LCR) (e.g., Wu and Wallace, Genomics 4, 560 (1989) and Landegren et al., Science 241, 1077 (1988)), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NABSA). (See, U.S. Pat. Nos. 5,409,818, 5,554,517, and 6,063,603). The latter two amplification methods include isothermal reactions based on isothermal transcription, which produce both single-stranded RNA (ssRNA) and double-stranded DNA (dsDNA) as the amplification products in a ratio of about 30 or 100 to 1, respectively.

Those having ordinary skill in the art, in light of this specification, will understand that many modifications, alternatives, and equivalents of the embodiments described above are possible. All such modifications, alternatives, and equivalents are intended to be encompassed herein.

EXAMPLES

The following procedures are representative examples of embodiments according to the disclosure that may be employed for the detection of a MAP organism. These examples are not intended to be limiting to the scope of the claims and/or the disclosure in any way.

Example 1: Compositions & Methods to Detect MAP Organisms

The present example describes exemplary assays designed to detect MAP organism using probe and primer sequences designed as described herein. The described assays can be used in diagnostic methods and kits to detect a MAP organism in a sample, such as for example a sample obtained from an animal suspected of being infected with a MAP organism, with no cross-reactivity to a non-MAP or other MAC organism.

A set of real-time qPCR primers and probes that can specifically amplify and detect the presence of *Mycobacterium avium* subsp. *paratuberculosis* without cross-reactivity with other subspecies in the *Mycobacterium avium* complex including *M. avium hominissuis*, and *M. avium avium* are described in Table 3 below.

Table 3 lists a set of TaqMan® primer/probe sets, where primer sequences comprise sets/pairs of primers, each primer set including a forward and a reverse primer, and a corresponding probe sequence, that have been shown to be specific to the amplification of MAP with a CT cutoff <38.

TABLE 3

| Assay ID No | Forward | Reverse | Probe | Coordinate on NC_002944.2 Left | Right | Locus | Product |
|---|---|---|---|---|---|---|---|
| 61801 | CGGTGCGCGGTAGGA SEQ ID NO: 6 | CGACCTGGTCTGCGTCATC SEQ ID NO: 7 | CCGCGAGGACCTGCTGACGC SEQ ID NO: 8 | 239559 | 239635 | MAP0225c | Hypothetical protein |
| 61802 | GCGATCCGGCGAAACG SEQ ID NO: 9 | GACGAGTTAGACGCACAGATTCT SEQ ID NO: 10 | ACGCCCTGCAGTTAGCTCCCCG SEQ ID NO: 11 | 239855 | 239922 | MAP0225c | Hypothetical protein |
| 61803 | ATCGACCGGCTGGTGTAC SEQ ID NO: 12 | GCGAGCAGCACGTTGAAC SEQ ID NO: 13 | TCGACGCGATGACCGCGCTCG SEQ ID NO: 14 | 240155 | 240255 | MAP0226 | Hypothetical protein |
| 61805 | CAGACACCTGCAGAGCTACTAC SEQ ID NO: 15 | AGCATGTCGGCGACGTT SEQ ID NO: 16 | CAAGCCCGACTACGCCGCCCT SEQ ID NO: 17 | 240712 | 240777 | MAP0226 | Hypothetical protein |
| 61808 | TCGCGGTGCCGATCAG SEQ ID NO: 18 | GTTTGGATGCCCGTGACATTC SEQ ID NO: 19 | CCGCGCTCCCCGAAATGCTC SEQ ID NO: 20 | 3088984 | 3089043 | MAP2756c | Large hypothetical protein |
| 61813 | CGGCGAACCCGTGACA SEQ ID NO: 21 | CACAGGTGCTCCCATTGAGT SEQ ID NO: 22 | CCGCGCCCAGCGTGTAGGC SEQ ID NO: 23 | 4168688 | 4168782 | MAP3740 | Large hypothetical protein |
| 61815 | GCGCAGCTTCACCATCGA SEQ ID NO: 24 | GTGCGAAGGCTTCGAAGAC SEQ ID NO: 25 | AACAGGCTGCCGCCACGCT SEQ ID NO: 26 | 4169324 | 4169424 | MAP3740 | Large hypothetical protein |
| 61816 | GCCACGACGGTGACATCA SEQ ID NO: 27 | CCAGGGTGCTGGTGAACA SEQ ID NO: 28 | CCGCGTTGCGGCCAGCCCG SEQ ID NO: 29 | 4169626 | 4169706 | MAP3740 | Large hypothetical protein |
| 61817 | GGAATCGATCTCGGTGGCTTTT SEQ ID NO: 30 | CCACCGCCGGAGCAA SEQ ID NO: 31 | CCGCGTGGCGCCGCA SEQ ID NO: 32 | 4169849 | 4169946 | MAP3740 | Large hypothetical protein |
| 61819 | GCCGCGACGGTAGGT SEQ ID NO: 33 | CCAGATCTCGGCAAGCGT SEQ ID NO: 34 | ACGACGCCGGCACAGCC SEQ ID NO: 35 | 4170784 | 417072 | MAP3740 | Large hypothetical protein |
| 61822 | CGGACGGAGAGGTGGAC SEQ ID NO: 36 | GGGCTCCGGCACCA SEQ ID NO: 37 | TTGCCGACCCGCAGACCTG SEQ ID NO: 38 | 4174593 | 4174666 | MAP3742 | Large hypothetical protein |
| 61823 | GGTAACCAGCAACCCGATCTG SEQ ID NO: 39 | CCCGAGGTGAACCACTTTGA SEQ ID NO: 40 | TCGGTTGATGATTTCACCCCAGGACGC SEQ ID NO: 41 | 4194693 | 4194779 | MAP3756c | Hypothetical protein |
| 61825 | GGCGTCCTCCGAACCA SEQ ID NO: 42 | GCAACATTGGCGATCGACATC SEQ ID NO: 43 | CAGCGGAGCATCACCGACCCCGG SEQ ID NO: 44 | 4195499 | 4195561 | MAP3757c | Hypothetical protein |
| 61826 | GGCTCGGGCCTGATAGC SEQID NO: 45 | GCGGCCTGAACTCCTATGATC SEQ ID NO: 46 | CCGCGTTCAGTGCCGTGGCC SEQ ID NO: 47 | 4195904 | 4195980 | MAP3757c | Hypothetical protein |
| 61829 | GCAATACTCGTGAACCGTAAACTG SEQ ID NO: 48 | GTGGCGCGGGTGTTG SEQ ID NO: 49 | CCCTGGCGGGCATTTCCTCTACG SEQ ID NO: 50 | 4196988 | 4197054 | MAP3758c-MAP3759c | Intergenic |

*Assay ID describes an assay comprising using Forward Primers and Reverse Primers described in one row and in some embodiments Probe described in the same row.

An exemplary method of detecting the presence of a MAP organism in a sample comprises: 1) isolating nucleic acid from a sample suspected to contain MAP and 2) detecting the presence of at least one MAP-specific target nucleic acid and/or fragment thereof and/or complement thereof as shown using an assay described in Table 3 above comprising using for example a set of primers, comprising a forward and a reverse primer described in a row to amplify the at least one MAP-specific target nucleic acid and/or fragment and/or complement thereof; and detecting the amplified product. In some optional embodiments, a probe described in the same row can be used to detect an amplified product amplified by forward and reverse primers from the same row. Such a method can be a diagnostic method, where a sample is derived from a mammalian animal suspected of being infected with a MAP organism. A diagnostic method can be used for example to diagnose a MAP related/caused disease or condition, such as but not limited to Johne's disease and/or Crohn's disease, by detecting the presence of a MAP organism in a sample derived from a mammal suspected of having this disease.

As shown in Table 3, an Assay ID number (such as 61801, 61802 etc.) is assigned to describe an associated primer pair and associated probes that can be used for amplification and/or detection of a target MAP sequence (such as in non-limiting examples SEQ ID. NOs: 1-5, Table 1) and/or fragments and/or complements thereof. These specific combinations of primer pairs and probe sequences have been designed to selectively amplify MAP specific target nucleic acid sequences. In some embodiments these primer pairs are degenerate.

In some embodiments, multiplex assays may be performed by simultaneously contacting a sample with the one or more primer pairs. Multiplex assays of the disclosure can be performed in parallel or sequentially.

Each of the assays was tested against the 16 sequenced *Mycobacterium avium* strains to confirm diagnostic sensitivity and specificity. For every assay the forward primer, reverse primer and probe were diluted in a mix to 900 nM for each primer and 250 nM for the probe (final, 1×, concentration). 8 µL of sample DNA (18-39 ng) was input into a 25 µL qPCR using the Path-ID™ qPCR master mix and each candidate MAP assay. The thermal profile and qPCR set-up is shown below in Table 4.

TABLE 4

| MAP AgPath-ID Master Mix | | | | |
|---|---|---|---|---|
| 25 | ul | reaction volume | | |
| 1X | | Component | 100 | rxns |
| 5 | ul | Sample | 500 | ul |
| 8.50 | ul | NF H20 | 850 | ul |
| 12.50 | ul | 2X Path-ID PCR Master Mix | 1250 | ul |
| 1.00 | ul | 26X MAP Primer Probe Mix | 100 | ul |
| Thermal Profile | | | | |
| 1. | | 95 dC: 10 mins: 1 Rep | | |
| 2. | | 95 dC: 15 sec | | |
| | | 80 dC: 80 sec | | |
| | | 40 Reps | | |

Table 5, below, has results of sensitivity and specificity testing. There was no cross-reactivity with any other non-MAP species (with a CT cutoff <38 considered positive).

TABLE 5

| | Sample Info | | | | | | | |
|---|---|---|---|---|---|---|---|---|
| Assay ID No. | Wood pigeon *M. silvaticum* ATCC 49884 | Asian Elephant MAA 10-5581 | Red Tailed Hawk MAA 10-9275 | Ruddy Duck MAA 11-4751 | Avian broadbill *M. avium* 05-4293 | White lipped deer MAH 10-4249 | Pig MAH 10-5606 | Pig Intermediate sp. MAC 10-5560 |
| 61801 | 40.00 | 40.00 | 40.00 | 40.00 | 40.00 | 40.00 | 40.00 | 40.00 |
| 61802 | 40.00 | 40.00 | 40.00 | 40.00 | 40.00 | 40.00 | 40.00 | 40.00 |
| 61803 | 40.00 | 40.00 | 40.00 | 40.00 | 40.00 | 40.00 | 40.00 | 40.00 |
| 61805 | 40.00 | 40.00 | 40.00 | 40.00 | 40.00 | 40.00 | 40.00 | 40.00 |
| 61808 | 40.00 | 40.00 | 40.00 | 40.00 | 40.00 | 40.00 | 40.00 | 40.00 |
| 61813 | 40.00 | 40.00 | 40.00 | 40.00 | 40.00 | 40.00 | 40.00 | 40.00 |
| 61815 | 40.00 | 40.00 | 40.00 | 40.00 | 40.00 | 40.00 | 40.00 | 40.00 |
| 61816 | 40.00 | 40.00 | 40.00 | 40.00 | 40.00 | 40.00 | 40.00 | 40.00 |
| 61817 | 40.00 | 40.00 | 40.00 | 40.00 | 40.00 | 40.00 | 40.00 | 40.00 |
| 61819 | 40.00 | 40.00 | 40.00 | 40.00 | 40.00 | 40.00 | 39.76 | 40.00 |
| 61822 | 40.00 | 40.00 | 40.00 | 40.00 | 40.00 | 40.00 | 40.00 | 40.00 |
| 61823 | 40.00 | 40.00 | 40.00 | 40.00 | 40.00 | 40.00 | 40.00 | 40.00 |
| 61825 | 40.00 | 40.00 | 40.00 | 40.00 | 40.00 | 40.00 | 40.00 | 40.00 |
| 61826 | 40.00 | 40.00 | 40.00 | 40.00 | 40.00 | 40.00 | 40.00 | 40.00 |
| 61829 | 40.00 | 40.00 | 40.00 | 40.00 | 40.00 | 40.00 | 40.00 | 40.00 |

| | Sample Info | | | | | | | |
|---|---|---|---|---|---|---|---|---|
| Assay ID No. | Dog Intermediate sp MAC 09-5983 | deer Intermediate sp MAC 11-0986 | bison MAP 10-4404 | bison MAP 10-5975 | cattle MAP 10-5864 | cattle MAP 10-8425 | sheep MAP 08-8281 | sheep MAP 11-1786 |
| 61801 | 40.00 | 40.00 | 27.12 | 28.50 | 28.47 | 29.31 | 30.57 | 27.03 |
| 61802 | 40.00 | 40.00 | 20.10 | 21.17 | 20.30 | 21.15 | 22.04 | 20.68 |
| 61803 | 40.00 | 40.00 | 26.01 | 27.56 | 26.35 | 27.30 | 28.06 | 25.11 |
| 61805 | 40.00 | 40.00 | 19.73 | 20.12 | 19.60 | 20.69 | 21.49 | 20.09 |
| 61808 | 40.00 | 40.00 | 18.33 | 19.69 | 19.05 | 19.57 | 20.04 | 19.53 |

TABLE 5-continued

| | | | | | | | |
|---|---|---|---|---|---|---|---|
| 61813 | 40.00 | 40.00 | 29.65 | 30.04 | 29.86 | 30.88 | 31.10 | 29.91 |
| 61815 | 40.00 | 40.00 | 19.78 | 21.45 | 21.36 | 22.16 | 22.14 | 21.03 |
| 61816 | 40.00 | 40.00 | 21.03 | 22.30 | 21.21 | 23.19 | 22.74 | 21.11 |
| 61817 | 40.00 | 40.00 | 32.05 | 33.05 | 31.55 | 33.60 | 34.49 | 30.34 |
| 61819 | 40.00 | 40.00 | 26.62 | 25.74 | 28.12 | 27.34 | 28.55 | 27.02 |
| 61822 | 40.00 | 40.00 | 19.59 | 20.26 | 20.00 | 21.08 | 20.75 | 20.04 |
| 61823 | 40.00 | 40.00 | 19.31 | 20.06 | 19.83 | 20.33 | 20.27 | 20.28 |
| 61825 | 40.00 | 40.00 | 18.21 | 19.23 | 19.26 | 19.63 | 19.57 | 19.20 |
| 61826 | 40.00 | 40.00 | 20.73 | 21.02 | 22.59 | 23.12 | 22.45 | 21.58 |
| 61829 | 40.00 | 40.00 | 19.12 | 19.91 | 19.78 | 20.25 | 20.22 | 19.56 |

The above experiment demonstrates the feasibility of using any of the assays listed below as a specific and highly sensitive detection method for *Mycobacterium avium* subsp. *paratuberculosis*. In some embodiments, the disclosure provides a set of highly-specific TaqMan® assays for the detection of *Mycobacterium avium* subsp. *paratuberculosis*.

One or more advantages of the methods of the present disclosure are described in the following section. Each individual assay can independently serve as a highly-accurate diagnostic assay for MAP detection. Each assay has the advantage of targeting single-copy gene in the MAP genome instead of genomic insertion sequences that are utilized in other MAP detection assays. Insertion sequences have the capacity to mobilize between genomes and insert into new species, making them suboptimal for a species-specific assay.

The currently described assays and methods are able to detect MAP in multiple host species including sheep, cattle, and bison quickly and accurately with no cross-reactivity between very closely related *M. avium* subspecies making it ideal for veterinary diagnostics.

While the foregoing specification teaches the principles of the present invention, with examples provided for the purpose of illustration, it will be appreciated by one skilled in the art from reading this disclosure that various changes in form and detail can be made without departing from the spirit and scope of the invention. These methods are not limited to any particular type of sample or nucleic acid contained therein for e.g., total genome DNA, RNA, cDNA and the like may be analyzed using some or all of the methods disclosed in this disclosure. This disclosure provides powerful tools for analysis of complex nucleic acid samples. From experiment design to detection of MAP microbes, the above disclosure provides for fast, efficient and inexpensive methods for detection of pathogenic organisms.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

TABLE 6

SEQ ID NOs: 1-50

SEQ ID NO: 1
CGGGTGCGGATTGATCAGCCGCCCATGGGCCACCAGCGATCCGTGTTGCTTGAGCCGCTGGGTGCGGACGTTGACCTCGT
AGCCGAGCACCCCGTCGAGCTGGCCGAGTTGCTCGCGCAGGTAGCGGTACAGGTCGTCGGAATCTCGGCAGATGGCCACG
GCCATCAGGTTTTTGGATCCGCTTGTGGCGCCGGCGAAAGCAATCTGCGGATGGGCCGCGATACGTTCGCCGACCGTGTG
CACGTCGCGAGGCGCAACCGTGAGCTCACAGCATGGCGCTGAGGCGATGGCCGAGCCGTTCGGGTAGTACGTCGACGTCGT
AGACCAGGGCGCCGCAGGCCTCCAGCGCCGCGATCCGCCTGCTCACCCGCGCCACCGACCAACCGGTGCGCGCGGCCAGT
TGGGACTGCGGAGTGCGGCCGTCGTCGGCGAGCGCCGCGAGCAGCGGGCGGTCTTCGGCGGTGGGCCGGGACCGGTGAGT
TCCCGACTCCGGCTGGGCCCGCGCGGCCACGATCCGCTGCGCTTGCCGGTCCGAGAGCGCGCTGCCGTAGCCCGTCCAGG
GCGCGTTCACCGGGTCGCCGAACGAATGCAGCATCAGATCGATGCTGATGTCGGTGACCGCGGCGGTGCGCGGTAGGAGC
TGCGTCAGCAGGTCCTCGCGGGTGTCGCCCAGCGGCGCACGGATGACGCAGACCAGGTCGGTCCACCCCGCCAGCACATT
GGCGTGGGACACGTCGGGGCGTCGCACCAGCGCGTCGGCCAGCCGCGATATGCGGTCCGGCGCCGCACGGATGCGGCACA
CCCAGTCCGCGTCGCCATCGGCCCACCGGTTCTCCAGCCCGACGACGCGCACCACCCCGTCGCGGCGCAGCCGGTGATAC
CGCCGGGCGACCGTCTGCTCGGTGGCGCCCACCACGCTGGCGATCCGGCGAAACGAGACCCGGGGAGCTAACTGCAGGGC
GTGCAGAATCTGTGCGTCTAACTCGTCGGTCATCAGGAAAAGTATCCGCGTGGACAGGTCCAAGTGAGGATTTCAGGCCA
ATTTGGTCGCGGCGAGCGCAATTTCAACGCCTCCGCTGTCAGCCTGGAAGCTCGGCCTAAGGAGCGCTCACATGCACATC
GAAATCGGACTGCCCAGCCATATCGCCCACGTGCGGGGCGGCTGACCGTCGAGTGGGCCCGCCGGGCCGAACACCGCGG
CTTTGCCGGCCTGGCCGCGATCGACCGGCTGGTGTACCCGAGCCTCGACGCGATGACCGCGCTCGCGGTGGCCGCGGGCG
CGACCACCGGCATCGGGTTGACGTTCAACGTGCTGCTCGCTCCGCTGTACCCCGCGGTGCTGCTGGCCAAGCAGGTCATC
ACCCTCGCGGAGGCGTCCGGCGGCCGGCTGCGCCTGGGGCTGGGCGTCGGGAGCCGCTGCGACGACTACACCGCCGTCGG
CGTCGACTATCGGCGGCGCGGGCGCATTCTCGACGAGACGGCGGCGCTGCTGCGTGCCGCGTGTGAGGCCGAGGTGGTGA
CCGGCGACCAGCCGCTGTGCCCGGCGCCGGTGCGGATCCCGATCCTGTTCGGTGGACGGGCGGACGCGACGATCCGCCGC
GCCGTGACCGTCGGTGACGGCTGGACCGCCGGGGCGCTGCGCGATTACGCCAACCAGTCGGTGTTCGCCGAGCGGGTCCG
GGCGGCATGGGCGGCGCGGGGCCGCTCCGGACGGCCGTGGCTGCAGGCCAGCGTCAACTTCGCCTTCGGCGATGACGAGG
CCGTCGCCGCTGGCCGCAGACACCTGCAGAGCTACTACGGCTTCAAGCCCGACTACGCCGCCCTCAACGTCGCCGACATG
CTCACCACGCCGCAGGAGGCGGC

SEQ ID NO: 2
CCCGCACCGCCGGTCCTGCCGCCGGACAATGCCGCGTTGGCTTCGCCGGCTGCCGCCGTGACGCGGCCTTCGGCGGCGAC
TTCGGCGTCCGCGGCGGCCAGCACCTCGGCTTCACCTGCCATGGCCGCGGGGCCCATGTTGCGCATCGCCGTGCTGGCTG
TGGTGGCCTGGGTCTCGACGCTGAACAGCTTGTCCTTCAACATGCCCAGACCCGTCCCGATCGGTGACAGGATCGTCGAG
GCGATGTTGTAGCCCTTGATCGCCAACCATGCCGTGCCCATTGCACCCACACCGACGGTCACCGCATCCAGCAACGGCTT
GTGCTCGGTGAGCCAATGCGCCGACTCCCCAAGCACCCCAACGACTTCAGTCATCGCTGGCAGAAAGTCCTGGCCGATCT
CGATGCGGGCTGCGCTCAACGCCCCCTTGAAGTCCTTCATCTTGGCGTTGTAGGTCTCCTGGGATTCGGTGAATCCCTTG

TABLE 6-continued

SEQ ID NOs: 1-50

GTATTGCCCGCACCGTCGGCCTGCGCCTGACTGACCTCCTTGACCGCGGCAGCGGCTTTGGGCCCGTTCTCCCCGACCAA
CTGCAATACCGTCCGCAGATTGTCTTGGCCGCCGACCATGAGGGCCAGCGCTTGGATCATCGACTGGACATCACCCTTGC
CGGACTTGAGCTGATTGTTGAAGCCTGTCAATGCTTTTTCTTGGTTCCACCACTGCTCGACAAGGTTGGCTTCCTCAACG
CTCAAGCCGCCGCGGTCCTTGCGGAACTGCTTGTACGCCTCAGCATTGTTCTGGATCGCCGTCGCGACCGCCTGCGCCTG
CGCGGGCAGCTTCGAGAACATCTCATTAGCGCTGTCGGCCACCTGCTTGCTCTTGAACCAGGCGTCCAGCGTGACCATCC
CCGACGGGCCAAGCTTCGACTGGATCGTGTCATACAACAGGTTCGCGGTGCCGATCAGGCCGCGCTCCCCGAAATGCTCC
TGAATGTCACGGGCATCCAAACCGAGCTGTCCCATCTCCTGGGACATTTGCTGGGTTGGCTTGGCCAGCGACGTGATCGC
GTGCGTCATATTCTGGGTGGCCTGATCAGCACCCATACCCGACTGAGTGAGCATCGCCAACGACGCATACAGGTCATTGA
CGCTTTCACCAACTCCGGCCGCGACCGGCTCGACGTTGTGCAACGCCCCGCGAAGTCTTGCAGCGAAACCTTCGACAAC
CCACGGCCACATTCAATTTCGAGGTGACGTTGGCGGCCTGCTCGACCGGGATGTGGTAGTCGTGCATCGTGGTCGTGAC
CGCGCTGATCGTCTCGCCCAGGTCCGCGCCCTCTTCGGACGCAAGCTGCGCTGAAGCCGTCAACACCTTGATCGCATCAC
TGCCCCGATAGCCGGCCTTCTCGACACCCAGCGCAGCGTCCATCAGCTTTTGAGGCGCATAACCGACCACGCTCGACAGT
TTCAGCACGCCATCGCTGATCGCCTTCAGATTGGCCGGCGACTCCTCGGCCACCGTGTGCAGCCTCTGCAACGACTGCTG
GAAATTCCCCGCCGCATCAGTCGCCGAGACA

SEQ ID NO: 3

ACATCGGGTGGAGTGCGGGGAGATCGAGCACGCGCTGCGCGGCCACCCGCTGGTCGCCGCCGCGACGGTGGTCCCCATCC
ACAACTGCACTGCGCTGGGCGCCGGGATCGTCGTAACCGGCAGCGGCGCAGAGCAATTTGACGACTCCACACCCGGCGCG
CTGCGCGCCCATCTCGCCGTCCGACTCCCGCAGTACATGATCCCCAAGGTGTTCGTCTCATGCCCCGAGCTACCGCTCAC
CGCCAACGGCAAGGTCGACCGGGGCAAAATCGCGGCGCGCCTCGAAGCGGCCGCGCGGGCACCCCAGCCGCTCGACACGT
CATCCACCCTCACTGTGGTCGAGCGGCTGGTCGCCGAGGTCTGGTCCGATGTGCTGGGCGCGCCGATCACCGGCCGCGAG
GACAATTTCTTCGCCCAGGGCGGCGATAGCCTGCGCGCCACCGAAGCGGTCGCCCGACTGACGCGCAGGGGAGTGGCCGG
AGCGGAGGTGGGCCAGCTGCTCAGCCACCAGACGCTTGGGCAGTTCAGCGCGGCGTGTGCTCGCCGACCCGGCATCCG
AGGCATCCGAGTCGGCGGCCGATGTCGGCGAACCCGTGACACCGGGCGAGGGGTTCCCGCTCACCCGGTTGCAGCAGGCC
TACACGCTGGGCGCGGCCGGACTCAATGGGAGCACCTGTGCACCAACGTATTTCGCGGTGGTGCTGGCCGCCGCGCCCGA
GTCTGCCGGTATAGACCTGGATCGGTTTGCCCGTGTGGTCACCAGATGCGTCGACGAATTCGCGATGCTGCGGTGCGCGC
TGGACGCCGACACCACCCAACGGGTGCAGGTCGACGCCGGGCCGGTGCCCGTCCATGACCTTGATATACAAGACGACCCC
GACCTGTTACTGCGGCGCATGGCGGCCGCCCCGTTCGATCCGCATTCGGTTCCGGTGATCCAGTGCTTCGCACCGTCGAG
GTCACCCCGTCACGTCGGTCTGCTGATCAGCTATCTGGGCCTCGATGCCCGCAGCCTGTCCACCGTCGTCACCACGATCA
TCGCCGAATACCAGTCGCAACCCCGGCCGCGGCAGGTCGACCCGACCGCGGCGGTCTTCGCCCGGTTTGCCTCCGAAAGC
GCTTGGGGCGAAAACGATGTCGACAACAGCGTTGCCGGCCCTCCGCTGCTGCCGCTGCACGACCAGCGACGTGACCCCTT
CGAGCGGGTCACCTTCGCGCGGCGCAGCTTCACCATCGAAGAACAGGCTGCCGCCACGCTGCGTGAGCACGCCGCACCC
TCGGCGTCACCCCCACCGCGCTGGTCTTCGAAGCCTTCGCACATGCGCTGGCGTCGATCGGCGCCGGTCAGCGATTCGCG
GTGACAGTCCCCAAGTCGTACCGTCCCGACTACGCCCCGCGGACCGCGAGGTGTTGGGCAACTTCACCCGCCTGGCGCT
GTGCGAGGTCGACTACGGCGCCGTGAGACCGGGATCTGCCGAAGCGGTTGCCGCGGCGCAGCGGGAACTGTGGCGCGCGG
TGAGCCACGACGGTGACATCACCGGCGGGCTGGCCGCAACGCGACCGCGGGTGGCTACCCGTGGTGTTCACCAGCACC
CTGGGGCTCACCCATCAGGACGCCAGCGGGCTGACCAACGTGCGGACATTGACCCAGACCCCGGGCGTCTGGCTGGACTG
CCAGACCGAGGACGAGGTCGCCGGAATTCGTATGAGCTGGGACATAGCTACCAATGTGGTTGCCGCGGAATCGATCTCGG
TGGCTTTTTCCCGATTCGAGGAGGCGGTGCGGCGCCACGCGGGGCAAGCCGAGCCGCCGGGCACGGCCGTTGCTCCGGCG
GTGGGCG

SEQ ID NO: 4

AGTGGGCGAGCGCGGTGATCGCCGCCGCGCTGCGCCACTGCCGACCCGAGCAGGTGCTGCCGCAATACACCATGCTGGTG
CGGCGCTGGGAGGCACTGCGATACGTCCCCTCAGGATACGCCCGCTTCCGACGTCGAACGGGCGGCTCGCCGGTTGGCCGG
CATCGTCACCGGAGCCGTGTCACCCCAGACGCTGATCGGAGACCCGCAGCTGACGCCCGAGGCGCTGCTGCTGCGTGACG
ACCGCATGCGGATGGCCCTCGACGACCTGGCCGGGGCCATCTTCGGGCACGCGCGCACGCTGGGGCGGCGGCTTCGCGTC
GTGGAAGTCGGCTCCCGGACCGGCCTGATCACCGAACGGTTGACCGAGCTGGTGGGCGTGGTGGTCGAGGAATACTTGTG
CCTGGAGCCAAACCCGACGCTCGCCGGAATCGCCGCCGGGCGGCGCTTCCCGGCCCCGACCCGCCACGTCGACGCACCCG
ACGCGGCGTCGGGCGTCGACGTGGTGATCTGCTGTGGGTCGCTGCATCAGCTGCCCGACGCGGAGGCGGTCCTCGAGGCG
ATCACCGTGTCCGACGACGGTTGGCTGTGGATGGTGGAGAATTCCGAGGCCACCCAAGCGACGCTCATCAGCGCGGCCGT
TCTCGACCCCGGCCTGCTCGCGTCCGATTCGAAGACGCTGCGTCCGGCCGATCGGTGGTGGCGGCTCATCGCCGACCACG
GTTGGCGACGACGCACATGATCCAGGACGGACCCGGCCTCACGCTCATCGCGCACCCGCCGACAAGCCCGGCATGCCG
ACACCGCCGGCCGAACAGCGCCGCGACGGTAGGTGGTCGCGACCGGCTGTGCCGGCGTCGTCGCTGCCGACCGACGCCAC
GGTGGTGGCCACGCTTGCCGAGATCTGGCAGCGTCATCTCGCCATTCCAACACCCGGCGTCGACGACGACTTCTTCCTGC
TCGGCGGTGACAGCCTCGTCGCGACCCGGGTCTACGCCGACCTTCGGGCCGCCGGTTTCGGCCAACTCGCTTTCGTCGAC
CTGTTCAACCACTCGACGCTCGGTGAGCTCGCGGCACACGCCGGCCGCGCACCGGCCACCGGAAGTGTCGGTGGCGGCTGA
GTCGACCCGGGGCGGCACCCACGACCCGAACCGATTCCCGCTCACCGTCGTCAGAACGCGTATCGGGCCGGGCGAGAAG
GCGCGTTGATCCTCGGCGGCGTCGCCGCGCACTGCTACTTCGAGTTCGAGCTCGCGGACTTCGACCGGCCGAGATTCGAT
TCGGCCGCACGCCAACTCGTAGCACGCCACGCCGGACTGCGCACCACGGTGTCACCGGCGGGCACCGACGCGGCCTCCTC
GGGTGAGGTCGCCGTCGTGCACACCGCCGCGATCGAGCCCGTCGTGCGAGACCACGACGACGTGCGAGCCGCGATGCGCG
ACCAGATCATCGACTTGACGGCCCGCCCGGGCATCGACTTCGGGGTGCAAACCCGGCGACGGCGCACCGTCGTCGGC
ATCAGCATGGACAACACCATGCTCGACGGCGGCCAGCATGATGATCGCCCTGTCCGAACTCGATCACCTCTATCGCGGCGA
AACCGTTGACCAATTGCCGCCGCTGGAAACGTCTTTCGCGCACTACGTGGAACCACCCGGAGCTGCTGCCCGACGCCG
ACGAGGCGGTGCTGCCGCGGCTGGCCGCCAGCCGAGACTATTGGCGCGCACGCCTGCCATCTTTGCCGCCGGCGCCGAAA
TTGGCCGACATGTCACTGCTGTTCGAGATCGAGGAGCCGAGGTTCGAACGGGCAACCGCGACCATTCCCGCCGTCGACTG
GTCGCAGGTAACGCGATCGTGCCGTGCCGAGGGCGTCACCGTCGCGTCATTTCTGCTCGCCAACTATGCACGGGTGCTGT
CTCGGTGGTCGGGGACCGACCACTTCTGCATCAACGTCACGCTATTCGACCGCGACCCCGATGTCGTGGGGATCGAAAAC
GTCGTCGGAGATTTCACTTCCCTGGTGTTGTTGGAGTGCCGAGTCGATGAGCCCGCCTCGATCTGGGAGAGCGTGCGCGC
TCTGCAGCGGCAATTGATGACCGACCTGCCGCACCGCCGGCGCGGACGTGGCCGGTGGCCTGCAACGCGAACTGCTGCGGTTTC
ACGGCAAACCCGACGGCCGCGCTGTTTCCCGTCGTCTTCACCAGCGGGACTGGGCCTTGTCGACGCCTCGGCTCGGGCGGCG
GTCCGGTTCGCCGAACCGGTATTCGCCGCCTCGCAGACACCGCAGAGGTGTTGGACTTCCAGGTGTGGGAAAGCGCGGG
GGCGCTGAAGCTGTCGTGGGACTTCGTCAGTCAGGCGGTGTCGCCGGCCACCGCGCGCACTCAGCTCGAGTCGTTGGTGG
ACGGCATCACCGGTGTCGCCACACGCAGCCGCGATGCATCGAACACAAGTTGGGCGAGGGGCATCCAATGACGAGCTCCTG
CAACGTGTTTCGAGGATCTGCGCGTCCGCCCTGGGTCAGCCGAGGGTCGAACCTCACGACAATTTCTTCCAGCTCGGCGG
CGATTCGGTCAGCGCGACCAAGGTGGTCGAACAGATCGGCCGTGAGCTGTCAGCCTCGGCCACCCTTCGACTGCTGTTCG
CCAATCCGGTGATCGGCGACTTCGCCGCCAAAATCGCCGACACTGACAACGCCGACGAACCCGACCTGACCGTTGAGGAG
GGCATGTTATGACCGCGGCCGAGCTCGTCGACCACCTGCGGGGTATCGGCGTCCAACTGTGGGCCGACGGTGAGAATTTG
CGCTACCGAGCACCGCAACAAGTCCTCACCGCGGACCTGAAAGCTCAACTGGCGGCGGTCAAAACGGACGTGATTACCCT

TABLE 6-continued

SEQ ID NOs: 1-50

GCTGGCGGAAGAGACGACCCTGCTGCGCGCCGCAGGACCGGTTCGAGCCGTTTCCGCTCACCGACGTGCAAGCCGCAT
ATCTGGTCGGGCGCACGTCGGCGTTTCAGTGGGGCGGGGTAGGCTGCCACGGCTACGCCGAGTTCGCGGTCGACCACACC
GTGGCAACACCGAGCGCCGAGCAATATCGGGAGGCGTGGCGCAAGGTTGCCGACCGCCACGACATGTTGCGCTGCGTCGT
TCATCCCGAGGGGTATCAGGTGATATGCCCCGACGTGCCCGACGACGGGCTGGTCATCCATCAGTGTCACACGGTCGAAG
ACGTTGCCGGCGTACGTGCCGGGGTCACGGAACATCTGCGTAACCGGATATATCCGTGGGCGAAGCGCCGATGTATGAC
CTGGTGATCACGATGGGCCCTGACGACACCGTGGTCCATCTGTCCGTTGACCTGCTGATCGCCGACTTCGTCAGCATCTC
CATCCTGATGACCGACTTTCAGCAGTGCTTGCTTGACCCCGAATGCGACCTTGCGCCCGTCGATTTCAGCTTCCGCGACT
ACCTGCTGAATCTCGCTCGCGAGCGAAGCTCGGCCGCCGGTAGTGCCCGCCGGGAACGCGATCTCGCCTACTGGCGGGAT
CGGCTCGATCAGCTGCCGTCACCACTGTCGTTACCGGTGCTGCCCGACGACTAGACGCCGTCAGCGTCGCGGACGGCACC
GACCTTTTCACGGCGTTCGATGCGCCTGTCGGCCGAGCGTTTCGAGGTGCTCAGCCGGCGCGCGGCAGAGCACGGAGCGA
CCGTCAACGTCGCCATCGTGACGGCATTCAGCCGGGCCATCGCACGCTATGGCGATCGCGACCATTTCCTGCTGACCCTG
ACGACCATGGACCGCCACGCGTTCACTCCCGCCGTCGGGCAGTTGGTCGGGGATTTCACCGGCACCAGCGTGCTCGAAGT
CGATGTCCGCGACAGCGCACCTTCGCCGAACTGCTGCACGGCGTCGGTGATCGTCTTCGACGACATGGACCATTCGA
CCACCGGCGGCGTCAACGTCGCCCGGCTCCTGGGGCAGCGCGACGACGACCGAGGTGAGCAGACGCCCGTCGTGTTCACC
TCGACACTCGGCGCCACGACCCGAATCGACAGCGGCGACATCTTTGTTGCACCCGATTCAAGGTCGCGGTCTGAGCCA
GACTCCTCAGGTGCTGCTGGACTGTCAGGTCGCCGAAATCGACGGCATGCTTGAGGTCAACTGGGACACCCGCGATCAGG
CCGTGCCCGCCGAGGTCCTCGACCGCGCGTTCGCCGACTTCCGCCACGCCCTGGATCTGCTCAGCACCGACGCCTCGGCC
TGGCACCGGCCGCTATTGCCGGCCCAGCCCCCGAGACCACACCGGTCGAGGGGCCACGCACACACCATGAACCGGCGCT
GATCCATACCGGGTTCCTGCGCAACGTGCTGGTGACACCGGATGCCGTCGCCATCCGCCACGGTGATCGGGCCACCACGT
ACGCCGAATTGCTCGCTGCCGCGACCGCGGTGGCCGACACGCTGGCCGCGACGGGGGTGCGGCCGCGTGACTACGTCGGT
ATCCGGTTGCCGCAGGGCCCCGCCCAGATCGCGGCTCTCCTGGGCGCATTGCTGGCCCGGGCCGCCTATGTGCCGTTGGA
CGTCGGCTGGCCCACTCACCGCGTCGACCAGATCGCGGCCCAATGCTCGCTGGCAGCGCTGTGCGAGCCGGACGGAGAGG
TGGACCGGCTGCTTGCCGACCCGCAGACCTGGTCACCGCGCGCGGCGGTGGTGCCGGAGCCCCACAGCGAGGTGCT

SEQ ID NO: 5

CCGACTCCGGTAACCAGCAACCCGATCTGGGCTCGGTTGATGATTTCACCCCAGGACGCAAGGGCGCTCCAACCCTCAAA
GTGGTTCACCTCGGGCTGATGTGGGGACAACACGGGGCCGGCATCTGGTGGCCTTGTCAAAAACCGGTTCGTGAAAATGGT
CGTATCCAAAGATCAGGTCGGCCCCCATACATTCGGCTTGGATGACCGCGGCACGCCAGGTCCGGTAGTTCGGGGTCCCG
GCCGGCTGGATCTGAACACCAACGGAGGAGATCATTGCCCGCCACCCGGCTGTCGATCCCGCGAGGGTTGCAGTCGGTGG
GTGATCCAGTCGAGGATGATTGACTGGGTATCTGCCGTGTAGCCCATGTGCCCGGTGGCAAAGAACCGCGCCGATTTGGG
GGACCCGTGCTCGAGCAGCAGGTAGTAGTCGCTGATCGGGAATACGGTGTCGTGTAGCCCGTTGATGAGCAGCGTCTCAG
CGCAGGGCCGGTCCAGGATACCTTGGCGTACAAGGGACAGCTTCGGCGCGTAGTCCACCCATTGCTCGAAGGTGTCGCGC
CCAAATGCATAGGCGAGGGTCTCGGCCAGCTCGAAGGGGTACTCGCCTGATTGGGCCTGCTCGATCCACTCGGCGTCAAA
GCCATGGTCGATGCAGCCGCCTTGGCTGACCACACAGGCGAGGGAGTTCCGGTGGGTGTGGGCGATTTTGGCCGCCCAGT
AGCCACCGGTACTACCACCCCAATAGCCCACACCCGCCGGGTCGAGTTCGGGTCGCCCGGCGATCCACTCCAACACGGGG
GTGAACATTCGCTCGGCGTCCTCCGAACCAGCCAGCGGAGCATCACCGACCCCGGGGATGTCGATCGCCAATGTTGCGAC
GTTCCGGGCGAGCACCTGATCGGTGTGCATGTCTTCCTTGAAGGTGTCGATCCCGCCGAGACGAGCAATACAGGCAGCC
GGTCCGTCGCCTTCGGGACACGCAGATGGGCGATGATGCGGTCACCCTCCCGGGCCGCCCGGCGAACGGGATCTCGACA
CGCTCGATGGGGATGTCGAAGTACGGGATGCGCGCAGCAACATTTCCTGCGACTTGCGGTAGGCGCTCTTCTTACCGGC
CGAATTCATCGTCGGGTAGCGGGCCATGCGGTAGTAGCCATAGGCGCGCAAATAGTTTTCGTGTGCCACACTGGTGTCGC
CAATCTGTTCGGCTCTTCGGCTCGGGCCTGATAGCGTGCGGCCACGGCACTGAACGCGGCCGCCCAGGCGTCGCGATCA
TAGGAGTTCAGGCCGCTCAACACGCCCTGCACATCATCGGCGAGCGTGTACTGAAACGGATAAATTCCCGCCGTGGCCGA
GACCGCCATAGCGGCCATAGCTCGGTCACCGGTCGCGTGTGTCGCTTCACACGGCCAAGTTATGACCGCTCGCGGCTGCA
GATATTGGAGAAAACGGACATCTCACGCGTGCCGTGGGCGAGCCGCACCGGGAAGTTCTGTGGGAGCCGCTCCAGCCAGT
GCCAGGCATTCGCTGATCAGGTCGGGACTGATCGGCGTAACCCGCCTCGATCGCTAGATCGGCCCACCGGATTCGGTGATC
ACCGGCATGGATCAAATCCAGCAGCCGCTGGAACCGGAAAATCCGGCCAAGCCGCTTGGGGCCGAAGCCGACCGCGGCGT
CGAACCGACGGCGAAGCTGCCGCTCGCTCAACCCAACAGAGGAGGCGACATCCGAAACAGAGCGGGCCGGGTGGACACGC
AGCATCTCGATTGAGTGCGCCACTGGCTGATCGACCACGGGATCGATCTTGACCACATACCGCGCCAGCACCGCCGCCAA
TAATGCGACCCGTTGCCGAAAAGCGTTGGCCTCCAGCACATCCTCAGCCAATCCGGACGCGGATGTCCCGAACACCGAGT
CAACCCGGATCTGGGTATCTCTTAACTCGCTGACAGGATGGCCCAGCACCGCGGCGGCAGCACCCGGTCGTAACCGCAGA
CCGATCATCGCACCTTCGGTGCCCGCACATTGGTCGTAAAAGGTTGTGGCCGGACCAGAAACCATGACTGCGCCCTCGGC
GGTGACGAACAGATCGACGCAACCGTCCGGCATCACCCGCAGCGCCCCACCCGCGGTATTCGAGCGCACCCAGCCACAGT
CCACATACGGCGCGAGCGCACCCAAAGGTCGACACTCCAAATACCCGACCATCACGCTCACATTCAGCCAGGTCCTACGT
CGCTCCGCAACAAATTGGGCCGCAATCCTTCGAAGCCGCCCGGTCAGCGCAGACTCCCAGGCGGCAATACTCGTGAACCG
TAAACTGCGGCGTAGAGGAAATGCCCGCCAGGGCGCAACACCCGCGCACTTCGGCGAGAAAGCGTGACAGG

SEQ ID NO: 6:

CGGTGCGCGGTAGGA

SEQ ID NO: 7

CGACCTGGTCTGCGTCATC

SEQ ID NO: 8

CCGCGAGGACCTGCTGACGC

SEQ ID NO: 9

GCGATCCGGCGAAACG

SEQ ID NO: 10

GACGAGTTAGACGCACAGATTCT

SEQ ID NO: 11

ACGCCCTGCAGTTAGCTCCCCG

SEQ ID NO: 12

ATCGACCGGCTGGTGTAC

TABLE 6-continued

SEQ ID NOs: 1-50

| | |
|---|---|
| GCGAGCAGCACGTTGAAC | SEQ ID NO: 13 |
| TCGACGCGATGACCGCGCTCG | SEQ ID NO: 14 |
| CAGACACCTGCAGAGCTACTAC | SEQ ID NO: 15 |
| AGCATGTCGGCGACGTT | SEQ ID NO: 16 |
| CAAGCCCGACTACGCCGCCCT | SEQ ID NO: 17 |
| TCGCGGTGCCGATCAG | SEQ ID NO: 18 |
| GTTTGGATGCCCGTGACATTC | SEQ ID NO: 19 |
| CCGCGCTCCCCGAAATGCTC | SEQ ID NO: 20 |
| CGGCGAACCCGTGACA | SEQ ID NO: 21 |
| CACAGGTGCTCCCATTGAGT | SEQ ID NO: 22 |
| CCGCGCCCAGCGTGTAGGC | SEQ ID NO: 23 |
| GCGCAGCTTCACCATCGA | SEQ ID NO: 24 |
| GTGCGAAGGCTTCGAAGAC | SEQ ID NO: 25 |
| AACAGGCTGCCGCCACGCT | SEQ ID NO: 26 |
| GCCACGACGGTGACATCA | SEQ ID NO: 27 |
| CCAGGGTGCTGGTGAACA | SEQ ID NO: 28 |
| CCGCGTTGCGGCCAGCCCG | SEQ ID NO: 29 |
| GGAATCGATCTCGGTGGCTTTT | SEQ ID NO: 30 |
| CCACCGCCGGAGCAA | SEQ ID NO: 31 |
| CCGCGTGGCGCCGCA | SEQ ID NO: 32 |
| GCCGCGACGGTAGGT | SEQ ID NO: 33 |
| CCAGATCTCGGCAAGCGT | SEQ ID NO: 34 |
| ACGACGCCGGCACAGCC | SEQ ID NO: 35 |
| CGGACGGAGAGGTGGAC | SEQ ID NO: 36 |
| GGGCTCCGGCACCA | SEQ ID NO: 37 |
| TTGCCGACCCGCAGACCTG | SEQ ID NO: 38 |

TABLE 6-continued

SEQ ID NOs: 1-50

| | |
|---|---|
| GGTAACCAGCAACCCGATCTG | SEQ ID NO: 39 |
| CCCGAGGTGAACCACTTTGA | SEQ ID NO: 40 |
| TCGGTTGATGATTTCACCCCAGGACGC | SEQ ID NO: 41 |
| GGCGTCCTCCGAACCA | SEQ ID NO: 42 |
| GCAACATTGGCGATCGACATC | SEQ ID NO: 43 |
| CAGCGGAGCATCACCGACCCCGG | SEQ ID NO: 44 |
| GGCTCGGGCCTGATAGC | SEQ ID NO: 45 |
| GCGGCCTGAACTCCTATGATC | SEQ ID NO: 46 |
| CCGCGTTCAGTGCCGTGGCC | SEQ ID NO: 47 |
| GCAATACTCGTGAACCGTAAACTG | SEQ ID NO: 48 |
| GTGGCGCGGGTGTTG | SEQ ID NO: 49 |
| CCCTGGCGGGCATTTCCTCTACG | SEQ ID NO: 50 |

What is claimed is:
1. A set of oligonucleotide primers comprising: at least one forward primer and at least one reverse primer, that are operable to hybridize to a MAP-specific target nucleotide sequence that is present in a MAP microorganism and is absent from a non-MAP organism, the pair of primers operable for simultaneous use in a PCR process for the detection of a *Mycobacterium avium* subsp. *paratuberculosis* (MAP) microorganism wherein the primers comprise a label selected from a dye, a radioactive isotope, a chemiluminescent label, and an enzyme, wherein the at least one forward primer and the at least one reverse primer are selected from: SEQ ID NO: 6 and SEQ ID NO: 7; or SEQ ID NO: 9 and SEQ ID NO: 10; or SEQ ID NO: 12 and SEQ ID NO: 13; or SEQ ID NO: 15 and SEQ ID NO: 16; or SEQ ID NO: 18 and SEQ ID NO: 19; or SEQ ID NO: 21 and SEQ ID NO: 22; or SEQ ID NO: 24 and SEQ ID NO: 25; or SEQ ID NO: 27 and SEQ ID NO: 28; or SEQ ID NO: 30 and SEQ ID NO: 31; or SEQ ID NO: 33 and SEQ ID NO: 34; or SEQ ID NO: 36 and SEQ ID NO: 37; or SEQ ID NO: 39 and SEQ ID NO: 40; or SEQ ID NO: 42 and SEQ ID NO: 43; or SEQ ID NO: 45 and SEQ ID NO: 46; or SEQ ID NO: 48 and SEQ ID NO: 49; complements thereof and primers having about 90% identity to the foregoing sequences.

* * * * *